US005721106A

United States Patent [19]
Maggio et al.

[11] Patent Number: 5,721,106
[45] Date of Patent: Feb. 24, 1998

[54] IN VITRO METHOD FOR SCREENING β-AMYLOID DEPOSITION

[75] Inventors: John E. Maggio, Brookline, Mass.; Patrick W. Mantyh, Edina, Minn.

[73] Assignees: Regents of the University of Minnesota, Minneapolis, Minn.; President and Fellows of Harvard College, Boston, Mass.

[21] Appl. No.: 304,585

[22] Filed: Sep. 12, 1994

Related U.S. Application Data

[63] Continuation-in-part of Ser. No. 744,767, Aug. 13, 1991, Pat. No. 5,434,050.

[51] Int. Cl.$^6$ .................................................. G01N 33/53
[52] U.S. Cl. .......................... 435/7.8; 435/7.1; 435/7.9; 436/501; 436/504
[58] Field of Search ........................ 435/4, 7.1, 7.21, 435/7.8, 7.9; 436/501, 86, 504

[56] References Cited

U.S. PATENT DOCUMENTS

| | | |
|---|---|---|
| 4,666,829 | 5/1987 | Glenner et al. |
| 5,221,607 | 6/1993 | Cordell et al. |
| 5,434,050 | 7/1995 | Maggio et al. |

FOREIGN PATENT DOCUMENTS

| | | |
|---|---|---|
| 2 223 578 | 4/1990 | United Kingdom . |
| WO 90/05138 | 5/1990 | WIPO . |

OTHER PUBLICATIONS

J.D. Sipe, "Amyloidosis", *Annu. Rev. Biochem.*, 61, 947–975 (1992).
C.J. Allen, "Specificity, Sensitivity and Ability to Quantify Amyloid Deposits in Alzheimer Disease Brain Using Either Radioiodinated βA4, Thioflavin S, Congo Red or Anti–A4 Antibodies", *Society for Neurosciences*, 18, 732 (1992) (Abstract Only).
M. Allison; "New Laboratory Model for Alzheimer's", *Harvard Medical Area, Focus*, Cover page and p. 3 (May 28, 1992).
D. Allsop et al., "Immunohistochemical evidence for the derivation of a peptide ligand from the amyloid β–protein precursor of Alzheimer disease", *Proc. Natl. Acad. Sci. USA*, 85, 2790–2794 (Apr., 1988).
A.E. Bolton et al., "The Labelling of Proteins to High Specific Radioactives by Conjugation to a $^{125}$I–Containing Acylating Agent", *Biochem J.* 133, 529–539 (1973).
D. Burdick, et al., "Assembly and Aggregation Properties of Synthetic Alzheimer's A4/β Amyloid Peptide Analogs", *J. of Bio. Chem.*, 267, 546–554 (1992).
A. Bush et al., "Rpid Induction of Alzheimer Aβ Amyloid Formation by Zinc", *Science*, 265, 1464–1467 (Sep. 2, 1994).
J.E. Castano, et al., "In Vitro Formation of Amyloid Fibrils from Two Synthetic Peptides of Different Lenghths Homologous to Alzheimer's Disease β–Protein", *Biochem. Biophys. Res. Commun.*, 141, 782–789 (1986).

J. Clemens et al., "Implants Containing β–Amyloid Protein Are Not Neurotoxic to Young and Old Rat Brain", *Neurobiology of Aging*, 13, 581–586 (1992).
C.M. Deber, *Peptides, Structures and Function*, pp. 221–224 and 249–252, Pierce Chemical Company, rockford, Illinois (1985).
"Experiments Link Alzheimer's Condition and Zinc", *The New York Times Medical Science*, p. C3 (Sep. 6, 1994).
J.F. Flood et al., "Amnestic effects of mice of four synthetic peptides homologous to amyloid β protein from patients with Alzheimer disease", *Proc. Natl. Adad. Sci. USA*, 88, 3363–3366 (Apr., 1991).
D. Games et al., "Lack of Alzheimer Pathology After β–Amyloid Protein Injections in Rat Brain", *Neurobiology of Aging*13, 569–576 (1992).
Remington's, (18th Ed.); "Medical Applications of Radioisotopes," *Pharmaceutical Sciences*, 33, 634–635, 748–749, Ed. A. R. Gennaro (1990).
J.R. Ghilardi et al., "Specific Metals and Salts Promote or Inhibit β–Amyloid Deposition Onto Existing Plaques in Alzheimer Disease Brain", *Society of Neuroscience*, 18, 732 (1992). (Abstract Only).
M. Goedert et al., "Cloning and sequencing of the cDNA encoding an isoform of microtubule–associated protein tau containing four tandem repeats: differential expression of tau protein mRNAs in human brain", *The EMBO Journal*, 8, 393–399 (1989).
C. Haass et al., "Amyloid β–peptide is produced by cultured cells during normal metabolism", *Nature*, 359, 322–327 (Sep. 24, 1992).
K. Halverson et al., "Molecular Determinants of Amyloid Deposition in Alzheimer's Disease: Conformational Studies of Synthetic β–Protein Fragments", *Biochemistry*, 29, 2639–2644 (1990).
W.S. Hancock, *CRC Handbook of HPLC for the Separation of Amino Acids, Peptides, and Proteins* (vol. II), pp. 3–22, 279–286 and 303–312, CRC Press, Inc., Boca Raton, Florida (1984).
J. Hardy et al., "Amyloid deposition as the central event in the aetiology of Alzheimer's disease", *Trends Pharmacol.*, 12, 383–388 (1991).

(List continued on next page.)

*Primary Examiner*—Marianne P. Allen
*Assistant Examiner*—Patricia A. Duffy
*Attorney, Agent, or Firm*—Mueting, Raasch, Gebhardt & Schwappach, P.A.

[57] ABSTRACT

The present invention provides: a labelled β–amyloid peptide or active fragment; a composition including the labelled β–amyloid peptide or active fragment thereof and a pharmaceutical carrier; a method for identifying active fragments of β–amyloid peptide; a method for labelling the β–amyloid peptide or an active fragment thereof; methods of using the labelled peptide or peptide fragment for detecting or monitoring Alzheimer's disease in a patient; and methods for screening agents that enhance or inhibit β–amyloid aggregation or deposition onto tissue or other amyloid substance, such as silk.

9 Claims, 15 Drawing Sheets

OTHER PUBLICATIONS

P.N. Hawkins et al., "Diagnostic imaging of amyloidosis," *European Journal of Nuclear Medicine*, 15(8), 436 (Abstract No. 149) (1989).

C. Hilbich et al., "Aggregation and Secondary Structure of Synthetic Amyloid βA4 Peptides of Alzheimer's Disease", *J. Mol. Biol.*, 218, 149–163 (1991).

W.M. Hunter et al., "Preparation of Iodine–131 Labelled Human Growth Hormone of High Specific Activity", *Nature*, 194, 495–496 (May 5, 1962).

C. Joachim, et al., "Amyloid β–protein deposition in tissues other than brain in Alzheimer's disease", *Nature*, 341, 226–230 (Sep. 21, 1989).

J. Kaiser, "Alzheimer's: Could There Be a Zinc?", *Science*, 265, 1365 (Sep. 2, 1994).

J. Kang, et al., "The precursor of Alzheimer's disease amyloid A4 protein resembles a cell–surface receptor", *Nature*, 325, 733–736 (Feb. 19, 1987).

R. Katzman et al., "Advances in Alzheimer's disease", *The FASEB J.*, 5, 278–286 (Mar., 1991).

D.A. Kirshner et al., "Synthetic peptide homologous to β protein from Alzheimer disease forms amyloid–like fibrils in vitro", *Proc. Natl. Acad. Sci. USA*, 84, 6953–6957 (Oct., 1987).

J.-Y. Koh et al., "β–Amyloid protein increases the vulnerability of cultured cortical neurons to excitotoxic damage", *Brian Res.*, 533, 315–320 (1990).

K.S. Kosik, "Alzheimer plaques and tangles: advances on both fronts", *Trends Neurosc.*, 14, 218–219 (1991).

J. P. Lee et al., "Conformational Features of Plaque–Competent Amyloid Peptides", *Society of Neurosciences*, 20, 606 (1994) (Abtrasct Only).

J.E. Maggio et al., "Reversible in vitro growth of Alzheimer disease β–amyloid plaques by deposition of labeled amyloid peptide", *Proc. Natl. Acad. Sci. USA*, 89, 5462–5466 (Jun. 1992).

J.E. Maggio, "Tachykinins", *Ann. Rev. Neurosc.*, 11, 13–28 (1988).

P.W. Mantyh et al., "Low Concentrations of $^{125}$I–BA4 Deposit onto Both Plaques and a Non–Plaque Component in Alzheimer Disease Cerebral Cortex", *Society of Neuroscience*, 19, 1038 (1993) (Abstract Only).

P.W. Mantyh et al., "High Concentration of Aluminum or Iron Promote Aggregation of Human β–Amyloid Peptide", *Society of Neuroscience*, 18, 765 (1992) (Abstract Only).

P.W. Mantyh et al., "Distribution and Characterization of Amyloid β Protein Deposition in Normal Human and Alzheimer's Diseased Cerebral Cortex Using $^{125}$I–βAP$_{1-60}$ as the Radioligand", *Society of Neuroscience*, 17, 912 (1991) (Abstract Only).

P.W. Mantyh et al., "Aluminum Iron and Zinc Ions Promote Aggregation of Physiological Concentrations of β–Amyloid Peptide", *J. of Neurochemistry*, 61, 1171–1174 (1993).

P.W. Mantyh et al., "Reversible In Vitro Growth of Alzheimer Disease β–Amyloid Plaques", *Bulletin of Clinical Neurosciences*, 56, 73–85 (1991).

P.W. Mantyh et al., "Substance P receptor binding sites are expressed by glia in vivo neuronal injury", *Proc. Natl. Acad. Sci. USA*, 86, 5193–5197 (Jul. 1989).

G.R. Marshall, *Peptides, Chemistry and Biology*, pp. 198–201 (Beilan et al.), ESCOM Science Publishers, Netherlands (1988).

P.C. May et al., "β–Amyloid Peptide In Vitro Toxicity: Lot–to–Lot Variability"*Neurology of Aging*, 13, 605–607 (1992).

S.S. Mirra et al., "The Consortium to Establish a Registry for Alzheimer's Disease (CERAD). Part II. Standardization of the neuropathologic assessment of Alzheimer's disease", *Neurology*, 41, 479–486 (Apr., 1991).

J.C. Morris et al., "The Consortium to Establish a Registry for Alzheimer's disease (CERAD). Part I. Clinical and neuropsychological assessment of Alzheimer's disease", *Neurology*, 39, 1159–1165 (Sep., 1989).

B. Muller–Hill et al., "Molecular Biology of Alzheimer's Disease", *Ann. Rev. Biochem.*, 58, 287–307 (1989).

R.J. Perry, "Recent Advances in Neuropathology", *Br. Med. Bull.*, 42, 34–41 (1986).

M.B. Podlisny et al., "Synthetic Amyloid β–Protein Fails to Produce Specific Neuroxicity in Monkey Cerebral Cortex", *Neurobiology of Aging*, 13, 561–567 (1992).

D.L. Price et al., "Toxicity of Synthetic Aβ Peptides and Modeling of Alzheimer's Disease", *Neurobiology of Aging*, 13, 623–625 (1992).

N.K. Robakis et al., "Molecular cloning and characterization of a cDNA encoding the cerebrovascular and the neuride plaque amyloid peptides", *Proc. Natl. Acad. Sci. USA*, 84, 4190–4194 (Jun., 1987).

P. Rovero et al., "Solid–phase synthesis of neurokinin A antagonists", *Int. J. Peptide Protein Res.*, 37, 140–144 (1991).

D.H. Schlesinger, *Macromolecular Sequencing and Synthesis, Selected Methods and Applications*, pp. 153–220, Alan R. Liss, Inc., New York (1988).

D.J. Selkoe, "The Molecular Pathology of Alzheimer's Disease", *Neuron*, 6, 487–498 (Apr., 1991).

D.J. Selkoe, "Deciphering Alzheimer's Disease: The Amyloid Precursor Protein Yields New Clues", *Science*, 248, 1058–1060 (Jun., 1990).

D.J. Selkoe, "Biochemistry of Altered Brain Proteins in Alzheimer's Disease", *Ann. Rev. Neurosci.*, 12, 463–490 (1989).

P. Seubert et al., "Isolation and quantification of soluble Alzheimer's β–peptide from biological fluids", *Nature*, 359, 325–327 (Sep. 24, 1992).

J.E. Shively, "Microisolation of Biologically Active Polypeptides by Reverse–Phase Liquid Chromatography", *Methods of Protein Microcharaterization, A Practical Handbook*, pp. 3–88, Humana Press, Clifton, New Jersey (1986).

D. Stipp, "Massachusetts Study Suggests That Zinc May Help Trigger Alzheimer's Disease", *The Wall Street Journal*, p. A1 and B2 (Sep. 2, 1994).

J.M. Stewart et al., Solid–Phase Peptide Synthesis (2nd edition), pp. 74–103 and 147–168, Pierce Chemical Company, Rockford, Illinois (1984).

H. P. Too et al., "Radioimmunoassay of Tachykinins", *Meth. Neurosci.*, 6, 232–241 (1991).

H.P. Too and M.R. Hanley, "Solubilization and characterization of substance P–binding sites from chick brain membranes", *Biochem. J.*, 252, 545–551 (1988).

USA Today, Life, Lifeline, p. 1D (Jun. 15, 1992).

J.S. Whitson et al., "Amyloid β Protein Enhances the Survival of Hippocampal Neurons in Vitro", *Science*, 243, 1488–1490 (Mar., 1989).

C. Wong et al., "Neuritic plaques and cerebrovascular amyloid in Alzheimer disease are antigenically related", *Proc. Natl. Acad. Sci. USA*, 82, 8729–8732 (Dec., 1985).

B.A. Yankner et al., "Neurotrophic and Neurotoxic Effects of Amyloid β Protein: Reversal by Tachykinin Neuropeptides", *Science*, 250, 279–282 (Oct., 1990).

"Aggregation/Deposition of β-Amyloid in Alzheimer Disease," Abstract No. 1RO1AG11852–01A1 (P. W. Mantyh) awarded by the National Institute on Aging (FY : 1994).

"Aggregation/Deposition of β-Amyloid in Alzheimer's Disease," Abstract No. 96324 (P. W. Mantyh) awared by the Department of Veterans Affairs, Research and Development (Feb. 22, 1993).

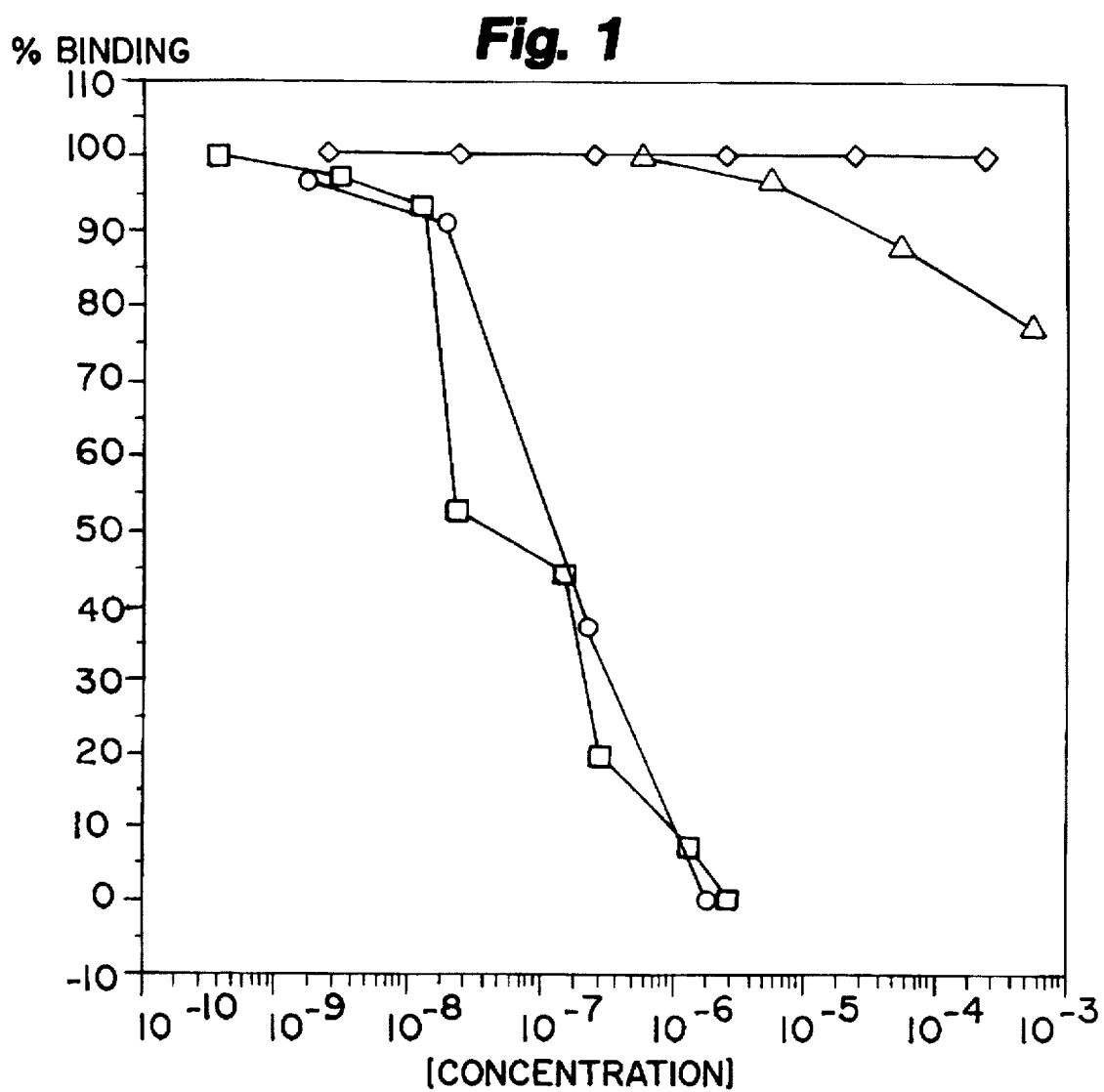

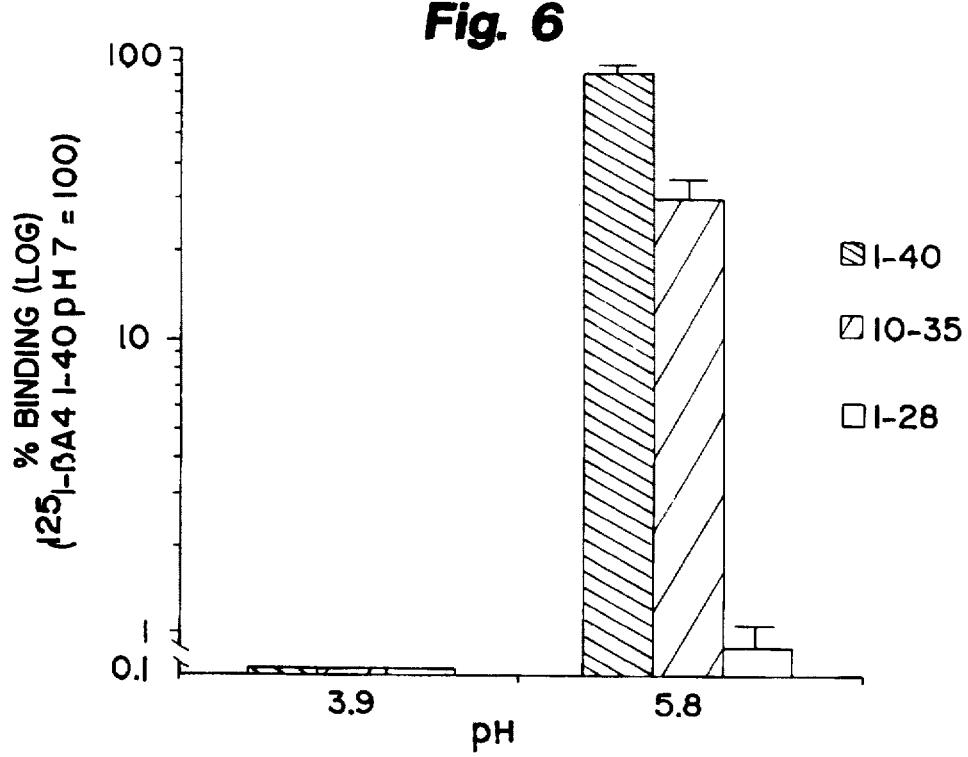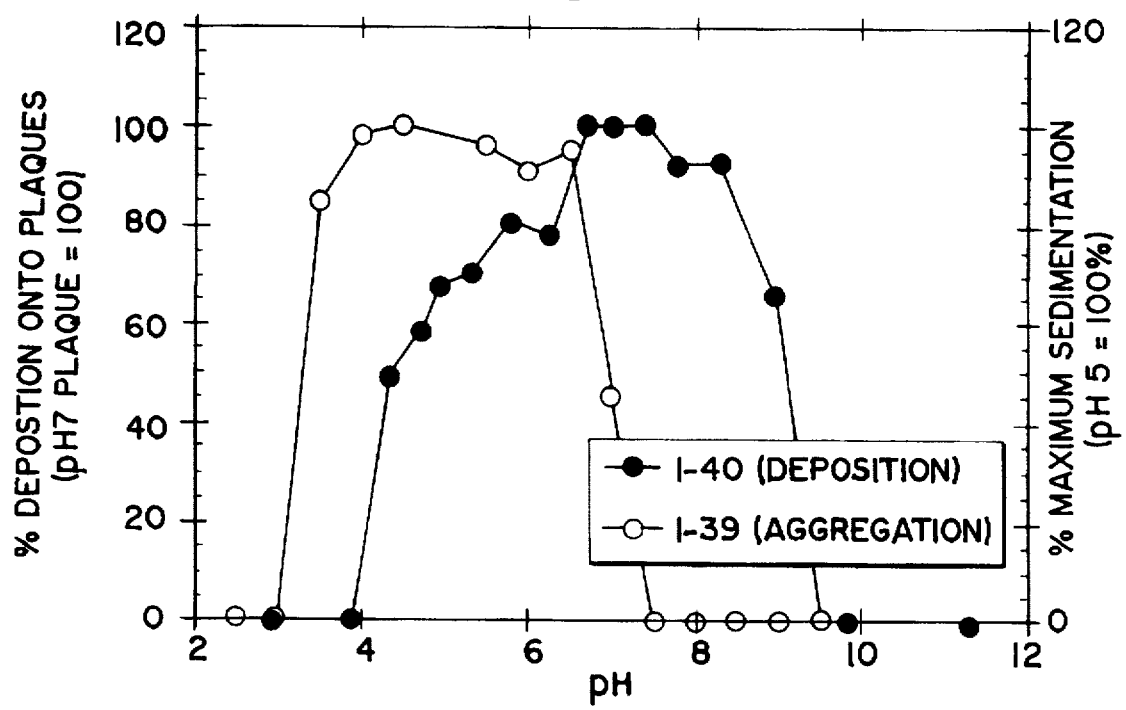

PHE20 Hβ1, Hβ2

ALA21β-METHYL

βA4 (10-35)-NH2

VAL18, Hβ, γ-METHYLS

ILLE31 Hγ Lγ2, δ-, γ-METHYLS

VAL18, Hβ, γ-METHYLS 3.8  2.5  2.0  1.5  1.0  0.5  ppa

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 40 amino acids
        ( B ) TYPE: amino acid
        ( C ) STRANDEDNESS: Not Relevant
        ( D ) TOPOLOGY: Not Relevant ( i i ) MOLECULE TYPE: peptide ( x i ) SEQUENCE DESCRIPTION: SEQ ID NO:1:

```
Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val
            35              40
```

( 2 ) INFORMATION FOR SEQ ID NO:2:

( i ) SEQUENCE CHARACTERISTICS:
        ( A ) LENGTH: 42 amino acids
        ( B ) TYPE: amino acid
        ( C ) STRANDEDNESS: Not Relevant
        ( D ) TOPOLOGY: Not Relevant ( i i ) MOLECULE TYPE: peptide ( x i ) SEQUENCE DESCRIPTION: SEQ ID NO:2:

```
Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
            35              40
```

( 2 ) INFORMATION FOR SEQ ID NO:3:

( i ) SEQUENCE CHARACTERISTICS:
        ( A ) LENGTH: 11 amino acids
        ( B ) TYPE: amino acid
        ( C ) STRANDEDNESS: Not Relevant
        ( D ) TOPOLOGY: Not Relevant ( i i ) MOLECULE TYPE: peptide ( x i ) SEQUENCE DESCRIPTION: SEQ ID NO:3:

```
Gly Ser Asn Lys Gly Ala Ile Ile Gly Leu Met
1               5                   10
```

( 2 ) INFORMATION FOR SEQ ID NO:4:

( i ) SEQUENCE CHARACTERISTICS:
        ( A ) LENGTH: 17 amino acids
        ( B ) TYPE: amino acid
        ( C ) STRANDEDNESS: Not Relevant
        ( D ) TOPOLOGY: Not Relevant ( i i ) MOLECULE TYPE: peptide ( x i ) SEQUENCE DESCRIPTION: SEQ ID NO:4:

```
Ser Asn Lys Gly Ala Ile Ile Gly Leu Met Val Gly Gly Val Val Ile
1               5                   10                  15

Ala
```

( 2 ) INFORMATION FOR SEQ ID NO:5:

( i ) SEQUENCE CHARACTERISTICS:
        ( A ) LENGTH: 39 amino acids
        ( B ) TYPE: amino acid
        ( C ) STRANDEDNESS: Not Relevant
        ( D ) TOPOLOGY: Not Relevant ( i i ) MOLECULE TYPE: peptide ( x i ) SEQUENCE DESCRIPTION: SEQ ID NO:5:

```
       Asp  Glu  Phe  Arg  His  Asp  Ser  Gly  Tyr  Glu  Val  His  His  Gln  Lys  Leu
       1              5                        10                       15

Val  Phe  Phe  Ala  Glu  Asp  Val  Gly  Ser  Asn  Lys  Gly  Ala  Ile  Ile  Gly
                      20                       25                       30

Leu  Met  Val  Gly  Gly  Val  Val
                 35
```

( 2 ) INFORMATION FOR SEQ ID NO:6:

( i ) SEQUENCE CHARACTERISTICS:
        ( A ) LENGTH: 35 amino acids
        ( B ) TYPE: amino acid
        ( C ) STRANDEDNESS: Not Relevant
        ( D ) TOPOLOGY: Not Relevant ( i i ) MOLECULE TYPE: peptide ( x i ) SEQUENCE DESCRIPTION: SEQ ID NO:6:

```
       Asp  Ala  Glu  Phe  Arg  His  Asp  Ser  Gly  Tyr  Glu  Val  His  His  Gln  Lys
       1              5                        10                       15

Leu  Val  Phe  Phe  Ala  Glu  Asp  Val  Gly  Ser  Asn  Lys  Gly  Ala  Ile  Ile
                      20                       25                       30

Gly  Leu  Met
                 35
```

( 2 ) INFORMATION FOR SEQ ID NO:7:

( i ) SEQUENCE CHARACTERISTICS:
        ( A ) LENGTH: 26 amino acids
        ( B ) TYPE: amino acid
        ( C ) STRANDEDNESS: Not Relevant
        ( D ) TOPOLOGY: Not Relevant ( i i ) MOLECULE TYPE: peptide ( x i ) SEQUENCE DESCRIPTION: SEQ ID NO:7:

```
       Tyr  Glu  Val  His  His  Gln  Lys  Leu  Val  Phe  Phe  Ala  Glu  Asp  Val  Gly
       1              5                        10                       15

Ser  Asn  Lys  Gly  Ala  Ile  Ile  Gly  Leu  Met
                      20                       25
```

( 2 ) INFORMATION FOR SEQ ID NO:8:

( i ) SEQUENCE CHARACTERISTICS:
        ( A ) LENGTH: 40 amino acids
        ( B ) TYPE: amino acid
        ( C ) STRANDEDNESS: Not Relevant
        ( D ) TOPOLOGY: Not Relevant ( i i ) MOLECULE TYPE: peptide ( x i ) SEQUENCE DESCRIPTION: SEQ ID NO:8:

```
       Asp  Ala  Glu  Phe  Arg  His  Asp  Ser  Gly  Tyr  Glu  Val  His  His  Gln  Lys
       1              5                        10                       15

Leu  Val  Phe  Phe  Ala  Gln  Asp  Val  Gly  Ser  Asn  Lys  Gly  Ala  Ile  Ile
                      20                       25                       30

Gly  Leu  Met  Val  Gly  Gly  Val  Val
                 35                       40
```

( 2 ) INFORMATION FOR SEQ ID NO:9:

( i ) SEQUENCE CHARACTERISTICS:
        ( A ) LENGTH: 4 amino acids
        ( B ) TYPE: amino acid
        ( C ) STRANDEDNESS: Not Relevant

```
        ( D ) TOPOLOGY: Not Relevant ( i i ) MOLECULE TYPE: peptide ( x i ) SEQUENCE DESCRIPTION: SEQ ID NO:9:

Tyr  Glu  Val  His
    1

( 2 ) INFORMATION FOR SEQ ID NO:10:

( i ) SEQUENCE CHARACTERISTICS:
        ( A ) LENGTH: 4 amino acids
        ( B ) TYPE: amino acid
        ( C ) STRANDEDNESS: Not Relevant
        ( D ) TOPOLOGY: Not Relevant ( i i ) MOLECULE TYPE: peptide ( x i ) SEQUENCE DESCRIPTION: SEQ ID NO:10:

Leu  Val  Phe  Phe
    1

( 2 ) INFORMATION FOR SEQ ID NO:11:

( i ) SEQUENCE CHARACTERISTICS:
        ( A ) LENGTH: 5 amino acids
        ( B ) TYPE: amino acid
        ( C ) STRANDEDNESS: Not Relevant
        ( D ) TOPOLOGY: Not Relevant ( i i ) MOLECULE TYPE: peptide ( x i ) SEQUENCE DESCRIPTION: SEQ ID NO:11:

Val  Gly  Asn  Ser  Lys
    1                     5

( 2 ) INFORMATION FOR SEQ ID NO:12:

( i ) SEQUENCE CHARACTERISTICS:
        ( A ) LENGTH: 7 amino acids
        ( B ) TYPE: amino acid
        ( C ) STRANDEDNESS: Not Relevant
        ( D ) TOPOLOGY: Not Relevant ( i i ) MOLECULE TYPE: peptide ( x i ) SEQUENCE DESCRIPTION: SEQ ID NO:12:

Gly  Ala  Ile  Ile  Gly  Leu  Met
    1                    5
```

IN VITRO METHOD FOR SCREENING β-AMYLOID DEPOSITION

CROSS-REFERENCE TO RELATED APPLICATION

This is a continuation-in-part of U.S. Ser. No. 07/744,767, filed Aug. 13, 1991 now U.S. Pat. No 5,434,050, which is incorporated herein by reference.

STATEMENT REGARDING GOVERNMENT RIGHTS

This invention was made with government support from the National Institutes of Health, NIH Grant Nos. NS-23970, NS-22961, and NS-26312. The government may have certain rights in this invention.

BACKGROUND OF THE INVENTION

Alzheimer's disease is a widespread progressive dementia affecting a significant fraction of the elderly population. While there have been significant advances in the research over about the last five years, the primary pathology of the disorder remains unknown. The behavioral symptoms of Alzheimer's disease are well known, and include loss of memory and cognitive function. The salient pathological symptom of Alzheimer's disease at autopsy is the presence in certain brain areas of extracellular proteinaceous deposits or plaques called amyloid on the basis of their staining with various reagents.

The extracellular amyloid is deposited both at neuronal and vascular sites, and the density of these deposits in the cerebral cortex and blood vessels correlates positively with the degree of dementia (D. J. Selkoe, *Neuron* 6:487 (1991); D. J. Selkoe, *Science* 248: 1058 (1990); B. Muller-Hill et al., *Ann. Rev. Biochem.* 58: 287 (1989); R. Katzman et al., *FASEB J.* 5: 278 (1991)). The principal component of both neuritic and vascular plaques in Alzheimer's disease is beta-amyloid peptide (β-amyloid or A4 peptide), a hydrophobic peptide of 39–43 amino acids which is encoded by a gene for a much larger protein termed the amyloid precursor protein (APP). Mature amyloid plaques have a halo of degenerating neurons around a core of the β-amyloid peptide (R. J. Perry, *Br. Med. Bull.* 42: 34–41 (1986). To date, neither the processing of APP to β-amyloid peptide nor the genesis of the amyloid deposits has been well understood. The characteristics of β-amyloid peptide deposition and the factors that affect it remain key questions in the pathology of Alzheimer's disease and other amyloidoses, such as reactive amyloidosis, familial amyloidotic polyneuropathy, insulinoma amyloidosis, senile cardiac amyloidosis, hemodialysis-associated amyloidosis, and Mediterranean fever.

At the present time, there is no established test other than brain biopsy for diagnosing Alzheimer's disease antemortem. Further, there is no system to quantify neuropathological changes associated with Alzheimer's disease. In addition, there is no method that has been developed to screen and evaluate agents that may have unique anti-amyloidosis action. There is also no method for in vitro evaluation of anti-amyloidosis agents, or of agents that may cause or enhance β-amyloid aggregation or plaque deposition, that does not require a sample of patient tissue. Indeed, no one has achieved Alzheimer's plaque growth in vitro under any conditions, and neither plaque growth nor amyloid aggregation behavior has been amenable to study under physiological conditions.

In view of the present lack of knowledge about the development and progression of Alzheimer's disease and other amyloidoses, there is a pressing need for agents and methods suitable for the diagnosis and detection of Alzheimer's disease and other amyloidoses. More particularly, there is a need for compounds and assay techniques that can be employed to screen for potential agents that inhibit or enhance the development of amyloid plaques, and especially for techniques that can be performed under physiologically relevant conditions. Such compounds and methods would be useful in assessing senile plaque formation associated with the onset and progression of Alzheimer's disease.

SUMMARY OF THE INVENTION

These and other objects are achieved by the present invention which is directed to a composition and method that is useful for studying, detecting and monitoring the progression of Alzheimer's disease in a patient. More specifically, the composition and method of the present invention are useful for detecting and quantitating amyloid aggregation and deposition in vivo and in vitro. Further, the present invention provides methods for screening and testing agents which inhibit or enhance amyloid aggregation or deposition onto human tissue.

The present invention provides a labelled β-amyloid peptide or labelled active fragment thereof useful for detecting Alzheimer's disease and studying Alzheimer's disease-related conditions. A method for obtaining the labelled β-amyloid peptide is also provided. The method employs essentially dry β-amyloid peptide and rapid formation of a labelled β-amyloid peptide. Preferably, the peptide has the amino acid sequence: H-DAEFRHDS-GYEVHHQKLVFFAEDVGSNKGAIIGLMVGGVV-OH [SEQ ID NO:1] or an active fragment of such amyloid peptide. In the preferred embodiment, the β-amyloid peptide is bound to a radioactive label such as radioactive iodine. However, other appropriate labelling agents and techniques, for example, enzymatic or fluorescent labelling of the β-amyloid peptide or active peptide fragment, can be used, either alone or in combination. The labelled peptide can be combined with a pharmaceutically acceptable carrier for in vivo diagnostic and possible therapeutic use.

Another embodiment of the invention provides a method for identifying active β-amyloid fragments. Active fragments are identified by their ability to deposit on Alzheimer's disease tissue or silk, which also contains amyloid structure. The present invention further relates to various uses of the labelled β-amyloid peptide or labelled active fragment thereof. One such use is in vitro detection and monitoring of Alzheimer's disease or other amyloidosis in a patient. This is accomplished by combining a sample of patient tissue with an amount of labelled β-amyloid peptide or active fragment thereof for a period of time effective to allow binding of the labelled peptide or peptide fragment to the tissue. The bound labelled peptide/tissue complex is then detected and, if desired, quantified. In vitro detection and monitoring can be accomplished by numerous techniques, including autoradiographic or homogenate binding assays. Further, progression of Alzheimer's disease or other amyloidosis may be monitored by assaying a later-acquired sample of tissue from a patient earlier tested in the same manner as the earlier-acquired sample. The amount of bound peptide or peptide fragment in the two tissue samples is compared to provide an assessment as to the development of the disease in a patient.

Homogenate binding assays can be used to screen for potential therapeutic agents, in particular, the ability of these agents to affect deposition of β-amyloid peptide onto tissue and existing plaques. This includes agents that inhibit or enhance deposition or are capable of breaking up existing plaques. An advantage of the present invention is that these screening assays are carried out using physiological (subnanomolar) concentrations of labelled β-amyloid peptide or labelled active fragment thereof. Carrying out drug screens under physiological conditions is much more likely to identify therapeutically useful drugs, and hence represents a significant advance over the prior art.

The invention further provides for the use of silk in place of tissue in the screening of drugs for their potential effect on amyloid deposition. This unexpected advance allows drug screening to proceed in the absence of the requirement of procuring diseased human tissue, thus reducing the cost of screening and making drug screening substantially more rapid and convenient.

According to the present invention in vivo detection of Alzheimer's disease in a patient is also possible by administering the labelled β-amyloid peptide or active fragment to the patient and detecting the presence of the labelled peptide or peptide fragment bound to the tissue in the patient by known imaging techniques such as positron emission tomography (PET) imaging.

Another aspect of the invention is an in vitro method for screening agents capable of affecting the aggregation of β-amyloid peptide. The method can be used to evaluate agents that inhibit or enhance aggregation. This includes an agent's ability to break up and, in certain cases, to inhibit formation or growth of plaques. Agents screened may be of potential use as therapeutic compositions for treatment of Alzheimer's disease or other amyloidosis. Screening of agents affecting β-amyloid peptide aggregation can be conducted in a test tube without plaque material. Thus, the present invention provides a technique for assessing agents that affect β-amyloid peptide aggregation that requires no patient tissue sample. In vitro screening of potentially useful anti-Alzheimer's disease agents is accomplished by combining β-amyloid peptide or an active peptide fragment thereof with the potential aggregation affecting agent to be screened in a solution. The amount of β-amyloid peptide aggregation is then detected and assessed to determine the effect of the agent on β-amyloid peptide or peptide fragment aggregation. This can be accomplished either in solution, or by filtration, centrifugation and the like. The aggregation affecting agent to be screened may be combined with the β-amyloid peptide or fragment thereof, either before, at or after the start of the peptide aggregation reaction. Alternatively, the β-amyloid peptide aggregation utilizes an aggregation enhancing agent (e.g., detergent, divalent metal cation) prior to inclusion of the aggregation affecting agent to be screened.

The present invention also provides an active β-amyloid peptide, βA(10–35)—NH$_2$, that is especially useful as a model for rational anti-amyloidosis drug design efforts.

The labelled β-amyloid peptide of the present invention and methods of use described herein provide qualitative and quantitative diagnostic tools for studying and potentially treating Alzheimer's disease and other amyloidoses. Use of β-amyloid peptide aggregation as a screening tool for compositions having potential therapeutic use provides a previously unavailable technique to study and evaluate potential therapeutic agents without patient tissue.

Other features and advantages of the invention will be apparent from the following detailed description and appended claims.

BRIEF DESCRIPTION OF THE DRAWINGS

FIG. 1 is a graphic representation of competitive inhibition of specific binding of $^{125}$I-β-amyloid peptide$^{1-40}$ ($^{125}$I-βA(1–40)-OH) by amyloid and tachykinin peptides in homogenates of Alzheimer's disease temporal cortex. LEGEND: □ β-amyloid peptide$^{1-40}$ (also known as β-AP$^{1-40}$, Aβ(1–40)-OH, βA4(1–40)-OH, or βA(1–40)-OH); ○ Dutch β-amyloid peptide$^{1-40}$; Δ β-amyloid peptide$^{25-35}$-NH$_2$ (βA(25–35)-NH$_2$); and ◊ Substance P, Neurokinin A, Neurokinin B, β-amyloid peptide$^{25-35}$-OH (βA(25–35)-NH$_2$), Rat β-amyloid peptide$^{1-40}$ (βA(1–40)-OH).

FIG. 6 is a histogram showing the pH dependence of plaque deposition of βA peptides at physiological concentrations onto AD plaques. Quantitative densitometry for autoradiograms at pH 3.9 and pH 5.8 are compared for $^{125}$I-βA(1–40)-OH, $^{125}$I-βA(10–35)-NH$_2$, and $^{125}$I-βA(1–28)-OH. All other conditions were identical. At pH 3.9 all three fragments were judged plaque-incompetent. In contrast, at pH 5.8 both $^{125}$βA(1–40)-OH and $^{125}$βA(10–35)-NH$_2$ were plaque-competent (83% and 30% respectively), while $^{125}$I-βA(1–28)-OH remained plaque-incompetent (<1%). [100%=deposition of $^{125}$I-βA(1–40)-OH at pH 7.4.] The pH dependence of deposition is significantly different from that of solubility or fibril assembly, which occurs only at much higher concentrations.

FIG. 7 is a chart showing deposition of $^{125}$I-βA(1–40)-OH at physiological concentrations (100 pM) onto plaques in AD tissue. There is a pH optimum around neutrality and activity extends over a wide range suitable for structural studies. Aggregation of amyloid peptides at 0.1 to 1 mM concentrations shows different pH profile, peaking around the isoelectric point of the peptide.

FIG. 12b is a comparison of aliphatic NOEs to the amide proton of Ala21. In the top trace an intra-residue NOE from the β-methyl group of Ala21 as well as inter-residue sequential NOEs from the β-methylene protons of Phe20 are observed for βA(1–28)OH. In contrast, the lower trace shows relatively stronger intra-residue and sequential inter-residue NOEs, as well as several new medium range NOEs (from the β-methine proton of Val18, both γ-methyl groups of Val18), and long range NOEs (from the γ-methylene protons and the γ-methyl or δ-methyl groups of Ile31).

DETAILED DESCRIPTION OF THE INVENTION

Figure 2A:
FIG. 2a–2h are an autoradiographic localization of $^{125}$I-β-amyloid peptide$^{1-40}$ ($^{125}$I-βA(1–40)-OH) binding sites in Alzheimer's disease brain, including controls and prior art techniques (demonstrating the superiority of the present invention).

The present invention provides: a labelled β-amyloid peptide or active (i.e., biologically, or chemically active, or shown as positive in an assay) fragment thereof; a composition including the labelled β-amyloid peptide or active fragment thereof and a pharmaceutical carrier; a method for labelling the β-amyloid peptide or an active fragment thereof; a method for identifying active β-amyloid fragments; and methods of using the labelled peptide or peptide fragment for detecting or monitoring Alzheimer's disease or other amyloidosis in a patient, and for screening drugs that may be of therapeutic value in the treatment of amyloidoses. The present invention further provides methods for using silk in place of tissue in the screening assays for identification of active β-amyloid fragments and for identification of agents that may affect amyloid deposition. Also provided is an isolated peptide fragment βA(10–35)-NH$_2$, which is of potential use in efforts to rationally design anti-amyloidosis drugs, since its three-dimensional structure can be used for computer-assisted drug design efforts.

As used herein, the term "aggregation" refers to the tendency of a molecule or colloidal body to associate together into a mass or body of units or parts. The term "deposition" refers to the tendancy of a material, e.g., a molecule or colloidal body, to associate with or adhere to a preexisting mass or body of units constituting a solid structure. In deposition, a material previously in solution deposits onto a preexisting structure, thus being removed from solution and forming a complex with the preexisting structure.

Labelled β-amyloid peptide or active fragments are used in the methods according to the invention. β-amyloid peptide has a sequence of about 40 amino acids. The exact length of the naturally occurring peptide may vary from about 39 to 43 amino acids, depending on the presence of ragged ends. The sequence of the 42-mer peptide is H-DAEFRHDSGYEVHHQKLVFFAEDVGSNKGAIIGL-MVGGVVIA-OH [SEQ ID NO:2], and the sequence of the 40-mer peptide is H-DAEFRHDSG-YEVHHQKLVFFAEDVGSNKGAIIGLMVGGVV-OH [SEQ ID NO:1]. The 40-mer peptide is preferred in the present invention. However, active fragments having as few as about 5 amino acids and ranging from about 5 to about 43 amino acid units are useful if appropriate labelling and measuring techniques are used to detect a smaller fragment of the 39- to 43-mer peptide. In particular, a peptide fragment derived from the 1–43 amino acid region of β-amyloid peptide and having at least 10 amino acid units, as for example, a fragment containing the amino acids at about position 25–35, may be used according to the invention.

As used herein, abbreviations for the amino acids are as listed in Table 1, as shown below. In addition, abbreviations for peptide termini are as follows: "H—" means a free amino group, "—OH" means a free carboxyl group, and "—NH$_2$" means a carboxyamide. Sequences are numbered from the amino termini with positions indicated by superscripts.

The β-amyloid peptide nomenclature used herein reflects the composition of the peptide and the chemical moiety at the C-terminus of the fragment. For example, βA(1–40)-OH) is the 40-mer (SEQ. ID NO:1) with a free carboxyl group at the C-terminus. βA(1–40)-NH$_2$ is the derivatized 40-mer, with a carboxyamide at the C-terminus. Alternatively, βA(1–40)-OH and βA(1–40)-NH$_2$ are referred to herein as β-amyloid peptide$^{1-40}$ and β-amyloid peptide$^{1-40}$—NH$_2$, respectively. As a further example, the C-terminal-carboxyamidated fragment consisting of residues 25–35 is referred to as βA(25–35)-NH$_2$ or alternatively, β-amyloid peptide$^{25-35}$—NH$_2$.

TABLE I

Amino Acid Codes

| Single Letter Code | 3-letter Code | Amino Acid |
|---|---|---|
| A | Ala | Alanine |
| C | Cys | Cysteine |
| D | Asp | Aspartic acid |
| E | Glu | Glutamic acid |
| F | Phe | Phenylalanine |
| G | Gly | Glycine |
| H | His | Histidine |
| I | Ile | Isoleucine |
| K | Lys | Lysine |
| L | Leu | Leucine |
| M | Met | Methionine |
| N | Asn | Asparagine |
| P | Pro | Proline |
| Q | Gln | Glutamine |
| R | Arg | Arginine |
| S | Ser | Serine |
| T | Thr | Threonine |
| V | Val | Valine |
| W | Trp | Tryptophan |
| Y | Tyr | Tyrosine |

The β-amyloid peptide or active fragment is combined with an acceptable label as described herein. The label can be radioactive, enzymatic, or fluorescent, or any combination thereof. Preferably, a radioactive label such as radioactive iodine-125 is used.

Among isotopes, any radioactive substance that may be incorporated into the peptide or peptide fragment may be used. Preferred isotopes include, but are not limited to, $^{125}$iodine, and $^{131}$iodine; the latter has a shorter half-life and higher energy level. Iodine radioisotopes may be incorporated into the peptide or peptide fragment by oxidative iodination. Also, radioactive iodine may be incorporated by use of Bolton-Hunter reagent to add a 3-iodo-4-hydroxyphenylpropionyl or 3,5-diiodo-4-hydroxypropionyl group to a nucleophile in the peptide.

Other isotopes may also be incorporated by reaction with nucleophile groups on peptides. For example, tritium ($^3$H) can be incorporated by reaction with propionyl-N-hydroxysuccinimide, or radioactive sulfur ($^{35}$S) can be incorporated by similar reagents. Radioactive phosphorus ($^{32}$P) may be incorporated by enzymatic methods. Additionally, various radioactive metal ions, such as $^{99m}$technetium, may be incorporated into β-amyloid peptide or fragments thereof if an appropriate chelating group is added first.

Preferably the method for obtaining purified labelled β-amyloid peptide or labelled peptide fragment thereof involves using a purified β-amyloid peptide or fragment thereof in dry form, i.e., lyophilized. This is then dissolved in a suitable reaction buffer and oxidative radioiodination is carried out to produce a labelled peptide or labelled peptide fragment (preferably monoiodinated), which is then isolated. Preferably, the concentration of the reaction buffer is above about 0.1M (more preferably about 0.5M sodium phosphate) and the pH is about 7–8 (more preferably about 7.5). It is preferred that the oxidative radioiodination take place rapidly; more preferably, the time between dissolving the peptide or peptide fragment in the reaction buffer and initiation of the isolation step is less than about two minutes, most preferably less than one minute. Also, it is preferred that the molar ratio of peptide or peptide fragment to radioactive iodine is greater than about 10:1. For labelled peptides or labelled peptide fragments that contain one or more oxidized methionine sidechains, it is particularly advantageous to reduce these sidechains after isolation of the labelled peptide or labelled peptide fragment, followed by isolation of the monoiodinated, reduced form of the labelled peptide or labelled peptide fragment. Preferably the reduction reaction is about 90 minutes or less.

For detection in in vitro assays according to the present invention, enzyme labelling is also useful. Among the preferred enzyme labels are peroxidases such as horseradish peroxidase (HRP), or phosphatases such as alkaline phosphatase.

Modifying the peptide or peptide fragment by adding an antigenic group that will bind with an antibody allows indirect detection of the peptide or peptide fragment itself. For example, the antigen digoxigenin can be linked to an oligonucleotide or peptide, and then visualized with a labelled digoxigenin-specific antibody, or labelled anti-antibody.

Although less sensitive than radioisotopes, fluorophores may also be incorporated into the peptide and detected according to known fluorescent detection techniques. Examples of suitable fluorophores include fluorescein, rhodamine, Texas Red, and the like.

Direct or indirect chemiluminescent labels may also be used according to the invention, such as dioxetanes. For example, the peptide would be modified with a group that is capable of emitting light as it decomposes.

In addition, an avidin-biotin system may be used to detect the peptide or peptide fragment in an in vitro assay. For example, the peptide or fragment may be functionalized with biotin, and avidin or streptavidin added to detect the peptide or fragment.

One embodiment of the invention provides a method for identifying active fragments of β-amyloid peptide. Fragments of β-amyloid peptide include peptides having all or part of the sequence of amino acids found in β-amyloid peptide, and further include derivatizations on the amino- or carboxy-terminal ends, such as amidation, or at other locations on the peptide. The fragments may be isolated from those peptides found naturally in the amyloid series, or, alternatively, synthesized in the laboratory or derivatized in the laboratory, as, for example, with C-terminal amidated peptide fragments. Polyethylene glycol (PEG) may be conjugated to peptides for pharmaceutical use to improve solubility, availability, lifetime, etc. Fragments further include β-amyloid peptides having substituted amino acids, as for example, a fragment containing glutamine instead of the wild-type glutamate at position 22 (e.g., Q22-βA(1–40)-OH). Alternatively, a fragment may be lacking a native amino acid altogether, which is indicated by the "Des-" prefix in the name (e.g., (des-A2)-βA(1–40)-OH, which is a 39-mer lacking the alanine at position 2).

Fragments labelled in accordance with the method described herein can be combined with amyloid plaque derived from Alzheimer's disease tissue or other amyloid substance such as silk, and tested for activity, for example, their ability to deposit on these materials. "Active" fragments are defined as those that show at least about 1% of the deposition activity of βA(1–40)-OH. Examples of active fragments of β-amyloid peptide include βA(26–42)-NH₂, (3-fold more active than β-amyloid peptide), βA(1–40)-OH, βA(1–40)-NH₂, βA(1–40)-PEG, (des-A2)-βA(1–40)-OH, βA(1–35)-NH₂, βA(10–35)-NH₂, βA(10–35)-OH, Q22-βA(1–40)-OH, also known as Dutch variant, familial AD, and βA(1–42)-OH. Fragments that are not active, i.e., that exhibit less than about 1% of the deposition level of βA(1–40)OH, include, for example, rat βA(1–40)-OH, PEG-βA(10–35)-NH₂, βA(1–28)-OH, β3A(25–35)-NH₂, βA(25–35)-OH, D27-βA(25–35)-OH, βA(40–1)-OH, and βA(11–25)-OH.

Figure 5:
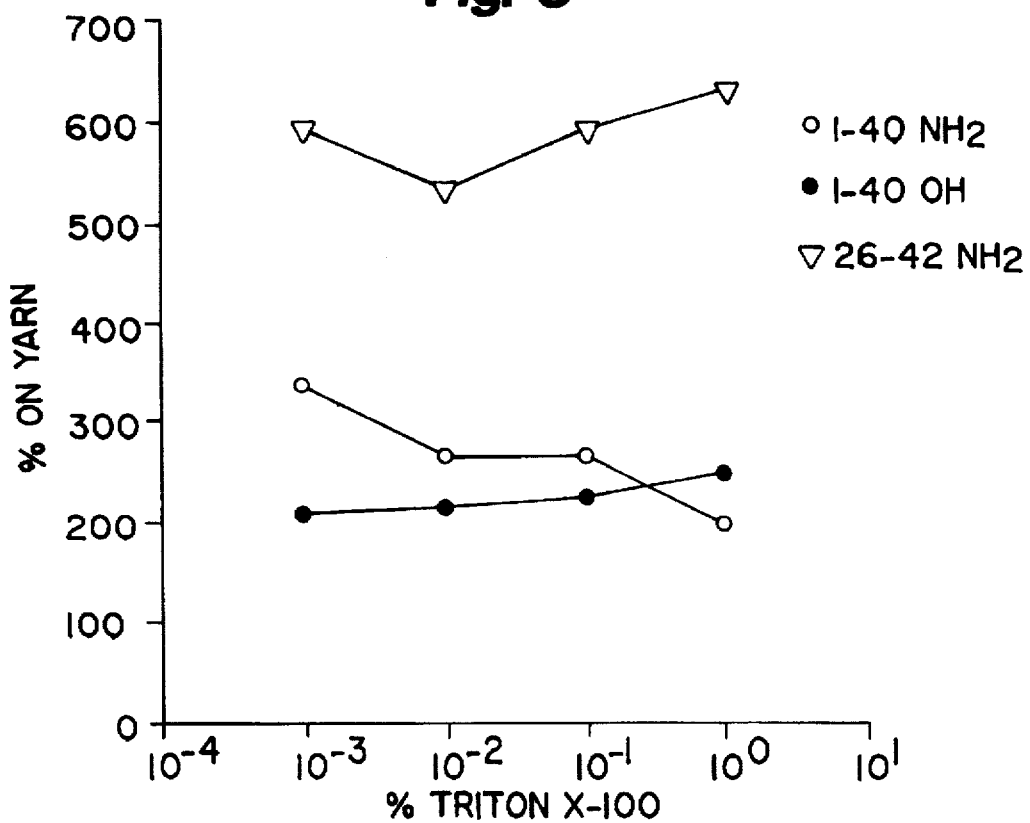
FIG. 5 is a chart showing deposition of radiolabelled peptide and peptide fragments onto ceilan katia yarn (silk), in the presence of Triton X-100, a nonionic detergent. All three peptides (βA(1–40)-OH, βA(1–40)-NH$_2$, and βA(26–42)-NH$_2$ are active, but βA(26–42)-NH$_2$ is three times more active than the others. The concentration of Triton X-100 (a nonionic detergent) had no effect on deposition rates.

The assay described herein is useful to establish activity. Once identified, such fragments can be used in place of naturally occurring β-amyloid peptides in diagnostic procedures and drug screening assays, and for further study into the basis for the pathology of Alzheimer's disease. Preferably, the active fragment βA(26–42)-NH₂ is used at least because it deposits about three times faster or more than β-amyloid peptide onto amyloid plaques (FIG. 5).

Also especially useful is fragment β-amyloid peptide$^{10-35}$-NH₂ [also known as βA(10–35)-NH₂], which displays about ⅓ the activity of βA(1–40)-OH, yet is small enough to make possible the determination of the first solution structure (i.e., the three-dimensional structure) of a β-amyloid peptide, solved via the application of nuclear magnetic spectroscopy (NMR). Previous attempts to obtain the solution structure of a β-amyloid peptide using the standard techniques of NMR and X-ray crystallography were not successful because of the peptide's low solubility and tendency to aggregate. Moreover, there was previously no consensus about which amyloid fragment to use for structural studies. The activity of βA(10–35)-NH₂ was something of a surprise, since earlier attempts to elucidate the important structural and functional features of β-amyloid peptide focused on the C-terminal or N-terminal ends of βA(1–40)-OH, neither of which is present in the peptide fragment βA(10–35)-NH₂. A problem with these earlier studies is that they were done at peptide concentrations $10^3$–$10^6$ higher (μM to mM) than that found physiologically, whereas the method of identifying active fragments described herein is carried out at physiological (subnanomolar) concentrations of peptide. Using the methods described herein, plaque competence for the peptide fragment βA(10–35)-NH₂ has been found to be associated instead with the folding of several residues about a conformationally restricted middle portion of the peptide backbone, found at hydrophobic residues Leu17-Val18-Phe19-Phe20 [SEQ ID NO:10].

The active peptide fragment βA(10–35)-NH₂ shows pH dependence similar to that exhibited by βA(1–40)-OH, (FIG. 6 and FIG. 7) and is folding- and plaque-competent. Thus, this fragment and the deduced solution structure is useful as a reasonable model system for investigating the amyloidogenic structure/activity relationship of the full length peptide, and can serve as a basis for the rational design of drugs to combat Alzheimer's disease and other amyloidosis-producing diseases.

In vitro methods of detecting amyloidoses, such as Alzheimer's disease, according to the present invention combine an amount of sample of tissue obtained from a patient with an amount of labelled β-amyloid peptide or labelled active fragment thereof. The tissue sample may be obtained from any tissue in which the growth of amyloid plaques may occur, including, for example, the nasal epithelium, skin and tissue obtained from portions of the brain such as the cerebral cortex, hippocampus and amygdala, and the like.

Preferably, the tissue sample used is about 1–20 μg/assay tube for tissue prepared in thin section which is preferably about 5–15 μm thick, and about 5–50 mg/assay tube for tissue prepared as a homogenate.

Submicrogram amounts (corresponding to physiologic, subnanomolar concentrations) of the labelled β-amyloid peptide or active fragment thereof, for example, about 0.1 to 10 nM of $^{125}$I radiolabelled β-amyloid peptide or fragment thereof, are added to each tissue sample for a time effective for the labelled peptide or peptide fragment to bind with the tissue sample. Preferably, the binding reaction time is about 1 to 5 hours, more preferably about 2 hours under the experimental conditions described herein. The time will vary depending on the specific experimental conditions, as will be understood by one skilled in the art. After reaction of the tissue sample with the labelled peptide or fragment, the tissue sample is preferably washed with an appropriate buffer to remove unbound labelled peptide. Homogenized tissue samples are preferably filtered prior to the washing step.

The assay preferably includes a negative control, for example, normal tissue in which binding of β-amyloid peptide is substantially negligible or about 10000 CPM (5% of the total isotope) under the experimental conditions described herein for homogenate binding assays, or less than about 25% of that exhibited in individuals with clinically diagnosed Alzheimer's disease (see Table II, below). The assay may further include a positive control of, for example, tissue that is positive for Alzheimer's disease.

Table II

Summary of clinicopathological features of control and Alzheimer's disease patients compared with the concentration of plaques detected with the $^{125}$I-β-amyloid peptide$^{1-40}$ technique.

For tissue with identification numbers (ID#) ending with "-D", the CERAD clinical, neuropsychological and neuropathological was used to confirm the diagnosis of Alzheimer's disease (J. C. Morris et al., Neurology 39: 1159 (1989); S.S. Mirra et al., Neurology 41: 479 (1991), the disclosures of which are incorporated by reference herein. The diagnosis of Alzheimer's disease for tissue with identification numbers (ID#) ending with "-R", was based on clinical assessment by the primary physician and neuropathological examination.

| ID # | Age/Sex | PM Interval[1] | Diagnosis[2] | Region[3] | P[4,6] | BV[5,6] |
|---|---|---|---|---|---|---|
| H 001-D | 76 yrs/F | 49 minutes | AD | T | ++++ | ++ |
| H 002-D | 84 yrs/F | 48 minutes | AD | F | ++++ | + |
| H 003-D | 79 yrs/M | 53 minutes | AD | T | ++++ | ++++ |
| H 004-D | 67 yrs/F | 25 minutes | AD | F,T | ++++ | − |
| H 005-D | 78 yrs/F | 46 minutes | AD | T | ++++ | ++ |
| H 006-D | 79 yrs/M | 63 minutes | AD | T | ++++ | + |
| H 017-R | 73 yrs/F | 13 hrs. 22 min. | AD | T | ++ | |
| H 020-R | 63 yrs/M | 5 hrs. 22 min. | AD | T | ++++ | + |
| H 023-R | 70 yrs/F | 5 hrs 30 min | AD | T | ++++ | |
| H 007-D | 59 yrs/F | 100 min. | Control | F,T | − | − |

-continued

| ID # | Age/Sex | PM Interval[1] | Diagnosis[2] | Region[3] | P[4,6] | BV[5,6] |
|---|---|---|---|---|---|---|
| H 008-D | 63 yrs/F | 103 min. | Control | T | – | – |
| H 009-D | 59 yrs/F | 80 min. | Control | T | – | – |
| H 010-D | 70 yrs/M | 135 min. | Control | T | – | – |
| H 019-R | 75 yrs/F | 10 hrs. 33 min. | Control | T | – | – |
| H 022-R | 63 yrs/M | 5 hrs. | Control | T | + | – |
| H 018-R | 75 yrs/M | 13 hrs. | AD/Parkins. | T | +++ | – |
| H 021-R | 60 yrs/M | 11 hrs. 20 min. | Parkins. | F | – | – |

[1]PM = post-mortem
[2]AD = Alzheimer's disease; Parkins. = Parkinson's disease.
[3]T = temporal cortex; F = frontal cortex.
[4]P = parenchyma of cerebral cortex.
[5]BV = blood vessel in cerebral cortex.
[6]concentration of plaques observed in P or BV: (–), not detectable; (+), light; (++), moderate; (+++), dense; (++++), very dense.

The in vitro detecting and monitoring techniques according to the present invention can be qualitative or quantitative. The presence of tissue-bound labelled peptide or peptide fragment may be detected according to known techniques appropriate for the particular labelling agent and method used (e.g., radioisotope, fluorophore, enzyme, antigen), the tissue sample type (e.g., homogenate, thin slice), the particular peptide or fragment used (e.g., β-amyloid peptide$^{1-40}$, β-amyloid peptide$^{25-35}$), and other factors of the assay. In addition, the method of detecting radioactive isotopes will vary according to the isotope and its corresponding energy level. For example, a gamma counter is capable of detecting $^{125}$iodine, but not tritium ($^3$H) or $^{35}$sulfur.

Where radiolabelling is used to label the peptide or fragment, the peptide/tissue complex may be detected by various known radioisotope detection techniques. For example, positron emission tomography may be used to detect isotopes that emit positrons such as radioactive $^{18}$fluorine or $^{11}$carbon, gamma counters to detect radioactive $^{125}$iodine, and scintillation counting methods in the case of tritium ($^3$H). Nuclear magnetic resonance imaging may also be used, in which case the label would contain a magnetically active particle.

Autoradiography is preferably used to visualize radiolabelled peptides or peptide fragments in tissue sections, and a radiation counter such as a gamma counter or scintillation counter preferred to detect radioisotopes in tissue samples prepared as a homogenate.

The in vitro detecting and monitoring techniques according to the present invention can also be used to monitor the progression of Alzheimer' disease in a patient. Later-acquired tissue samples may be assayed according to the method provided by the invention, and compared to the results of earlier assays of tissue from the same patient. A comparison of the amount of bound labelled peptide or labelled active peptide fragment detected in the two tissue samples provides a convenient assessment of the development of the disease in a patient.

In vivo detection and monitoring of Alzheimer' disease includes administering the labelled β-amyloid peptide or labelled active fragment thereof to a patient in an amount effective to bind with tissue evidencing the presence of, or susceptibility to, Alzheimer' disease. Like in vitro detecting methods, the presence of the labelled peptide or peptide fragment bound to tissue in the patient is detected by a known detecting technique that is appropriate to the tissue sample type, the particular peptide or fragment used, the labelling method used, and other such factors unique to the particular assay being performed.

For example, medical imaging can be used. For medical imaging, the label should be detectable outside of the body. Preferably, the label is a positron emitting radioisotope with a relatively short half-life, such as $^{11}$carbon or $^{18}$fluorine. Such an isotope may be imaged by positron emission tomography, or PET scanning. Magnetic resonance imaging may also be used, in which case the label would include a magnetically active particle.

The present invention also provides useful methods to detect, monitor and screen potential therapeutic agents for affecting Alzheimer'disease. In particular, methods for in vitro screening of agents that are capable of inhibiting or enhancing the aggregation of β-amyloid peptide or active fragments thereof, including the ability to break up and, in certain cases, to inhibit formation or growth of plaques, are provided.

One method is based on the finding that β-amyloid peptide will self-aggregate (i.e., aggregation of β-amyloid molecules based solely on concentration) in solution. This method is particularly advantageous since no patient tissue is required. The aggregation of β-amyloid peptide is dependent primarily on the concentration of the peptide or peptide fragment. For example, an about $10^{-4}$ molar aqueous buffer solution of β-amyloid peptide$^{1-40}$ will commence self-aggregation within a period of about 5 to 30 minutes. At lower concentrations, β-amyloid peptide aggregation may take from about 1 to 5 hours or longer.

Thus, in one embodiment of the invention providing a β-amyloid peptide aggregation screening test, labelled β-amyloid peptide or a peptide fragment thereof is combined with an acceptable buffer or solvent and a potential aggregation-affecting agent. The aggregation-affecting agent to be screened may either enhance or inhibit aggregation. Preferably, the reaction is conducted at about pH 5 to about pH 9. After a specified period, for example 1 to 2 hours, the amount of aggregation is determined. The amount of aggregation can also be periodically monitored over a set time period. More specifically, after a period of time effective to allow aggregation of the peptide or peptide fragment in the solution, for example, about 5 to 60, or preferably about 15 to 30 minutes, a potential aggregation-affecting agent is added. Alternatively, the aggregation-affecting agent to be screened may be added at or before the start of aggregation of the peptide. The inhibiting or enhancing effect of the agent is subsequently determined.

It may be desirable to enhance the aggregation of the peptide or fragment, in order, for example, to evaluate the effect of the aggregation-affecting agent at lower peptide concentrations. To enhance aggregation of the peptide or fragment, an aggregation enhancing or promoting agent may be combined with the peptide or peptide fragment prior to addition of the aggregation affecting agent. For example, the enhancing agent may be a small amount of pre-formed aggregate of the peptide or peptide fragment, an amount of amyloid plaque derived from Alzheimer'disease tissue or other amyloid substance, preferably silk, or other substance capable of expediting the aggregation, as for example, a metal ion, or a detergent. About 0.01 to 2% of a detergent such as digitonin, 3-[(3-cholamidopropyl) dimethylammonio]-1-propanesulfanate, also known as CHAPS, available from Sigma Chemical Company (St. Louis, Mo.), or octoxynol such as Triton X-100 available from Sigma Chemical Company (St. Louis, Mo.), but preferably an anionic detergent, such as sodium dodecylsulfate (SDS). An amount of about 0.1 to 50 millimolar of a metal ion, such as aluminum ($Al^{3+}$), zinc ($Zn^{2+}$), or iron ($Fe^{2+}$, $Fe^{3+}$), can also act as an aggregation-enhancing agent. The aggregation-enhancing agent is added to the peptide/fragment solution in an amount effective to initiate or promote aggregation of the peptide or peptide fragment. The aggregation reaction is preferably conducted at a pH of about 5 to about 9. Preferably, the peptide fragment concentration in the solution is less than about 1 nanomolar, corresponding to that found physiologically.

The aggregation assay described herein provides a technique to screen potential therapeutic agents. In an aggregation assay, the β-amyloid composition will contain the peptide or fragment in an amount effective to self-aggregate, or an amount of β-amyloid peptide together with the chosen aggregation enhancing agent.

In yet another embodiment, the invention provides a pharmaceutical composition for in vivo use in detecting Alzheimer's disease in a human tissue. The composition contains labelled β-amyloid peptide or active peptide fragment thereof, in a pharmaceutically acceptable carrier of the type appreciated by those of skill in the art. The composition contains the labelled peptide or peptide fragment in an amount effective to bind to tissue evidencing the presence of, or susceptibility to, Alzheimer's disease, when administered in vivo.

As described above, the labelled Iβ-amyloid peptide or labelled peptide fragment is useful to detect or quantify the presence of, or tissue susceptibility to, Alzheimer's disease or other amyloidoses in human tissue. In an in vitro tissue binding assay, the amount of labelled peptide or fragment used is an amount effective to bind with tissue evidencing the presence of, or susceptibility to, Alzheimer's disease or other amyloidoses. Such a tissue binding assay, conducted on homogenates of brain or other appropriate tissue obtained, for example, from patients with Alzheimer's disease, can be used to test agents that may be useful in diagnosis and treatment of various amyloidoses, such as Alzheimer's disease, and in, for example, anti-Alzheimer's disease compositions.

According to one method, potential therapeutic agents are placed on competition with labelled β-amyloid peptide or labelled peptide fragment thereof in a solution with sample patient tissue, and the effect of the test agent on β-amyloid peptide or peptide fragment binding to same tissue is quantified.

Specifically, labelled β-amyloid peptides or labelled active fragments thereof are combined with a tissue sample from a patient with Alzheimer's disease or other amyloidosis and a potential deposition-affecting agent, and the effect on deposition of labelled peptide or peptide fragment onto the tissue is observed. Preferably, the concentration of peptide or peptide fragment is below about 1 nM, which corresponds to a physiological concentration. The tissue sample and peptide or peptide fragment are preferably combined in an acceptable buffer or solvent, with a pH of about 5 to about 9. A deposition-enhancing agent may be added prior to the addition of the deposition-affecting agent to be tested. With respect to deposition of the labelled peptide on tissue plaques, an amount of about 0.1 to 50 millimolar of a metal ion such as manganese ($Mn^{+2}$) or zinc ($Zn^{+2}$) can act as an enhancing agent. For example, zinc chloride (0.1 mM) enhances the rate the rate of deposition of labelled peptide twenty-fold, whereas ethylene diamine tetraacetic acid (EDTA; Sigma Chemical Company, St. Louis, Mo.), a chelating agent (0.1 mM), inhibits the rate five-fold. With respect to detergents, anionic detergents, preferably sodium dodecyl sulfate (SDS), enhance deposition, whereas neutral detergents, such as Triton X-100 (Sigma Chemical Company, St. Louis, Mo.), or zwitterionic detergents, such as Zwittergent 312 (available from Calbiochem, San Diego, Cailf.), have no effect.

The present invention further provides for the use of silk as a substitute for human disease tissue in the in vitro evaluation of potential therapeutic agents affecting plaque growth. Preferably, it provides for the use of insect (e.g., silkworm) or spider silk. More preferably, commercially available silks, such as raw silk, organza, material tan pongee, doupioni cloth, or ceilan katia yarn are used. Ceilan katia yarn is most preferred. Silk is inexpensive, easily available, and convenient to use. Treatment with certain dye molecules (Congo red, thioflavin S), demonstrate that silk exhibits an amyloid structure (i.e., a particular ordered peptide structure with the polypeptide chains in a cross-beta conformation). The art in Alzheimer's disease research has focused on the plaques deposited in tissue of affected victims. A simpler, more cost-effective drug screen, involves the use of various silks as a model for plaque deposits. Surprisingly, radiolabelled β-amyloid peptides of the present invention bind to silk with great affinity, and in a way very similar to their binding to human AD (Alzheimer's disease) amyloid tissue. Among the properties that deposition onto silk and deposition onto authentic human AD plaques share are pH dependence, first order kinetics and high sensitivity. Deposition onto silk is carried out at an optimal pH, preferably between about pH 3 and about pH 8, more preferably about pH 5. The pH optimum for deposition onto AD tissue is somewhat higher (preferably between about pH 6.5 and pH 8.5), but the important point is that deposition onto AD tissue and onto silk both occur at physiological pH (pH 6–9), and both show a qualitatively similar pH dependence.

Thus, another embodiment of the invention involves using silk instead of tissue in the screening assay for agents capable of affecting amyloid deposition. The invention also provides for the use of silk instead of tissue in a method of identifying active fragments of β-amyloid peptide.

The use of commercially available silk in place of AD plaques in the tissue deposition assay provided by this invention offers a convenient and inexpensive way to screen for compounds that block deposition and thereby inhibit amyloidosis. Because the silk assay is conducted in standard 96 well plates, it is easily automated and can be performed by industrial robots. For example, using 20 pM $^{125}$I-βA (1–40)-OH as tracer, and 0.5 mg silk as template, several thousand counts can be deposited in two hours. In contrast, typically 100 pM radiolabelled tracer and 5 mg tissue is used in the brain homogenate assay. The silk model may also prove useful in the study, diagnosis and treatment of numerous other known non-Alzheimer's human amyloidoses, such as reactive amyloidosis, familial amyloidotic polyneuropathy, insulinoma amyloidosis, senile cardiac amyloidosis, hemodialysis-associated amyloidosis, and Mediterranean fever.

As noted above, both self-aggregation of β-amyloid peptide and deposition of peptide onto tissue or silk are pH dependent. A surprising finding was that the pH profiles for aggregation and deposition differ. This finding was obtainable only by virtue of the methods described in the present invention, insofar as such methods allow investigation of β-amyloid peptide deposition at physiological concentrations of the peptide. Aggregation reactions are conducted at a pH that optimizes peptide aggregation, generally between about pH 3 and about pH 8, preferably between about pH 4 and about pH 6. Deposition reactions are conducted at a pH that optimizes peptide deposition, which for tissue is generally between about pH 5 and about pH 9, more preferably between about pH 6.5 and about pH 8.5. See FIG. 7.

Thus, a very important and useful aspect of this invention is that it allows medical diagnosis and drug screening for Alzheimer's disease and other amyloidosis-producing diseases to be carried out at physiological, i.e., subnanomolar, concentrations of β-amyloid peptide. For instance, drugs that affect aggregation behavior at high concentrations of the β-amyloid peptide may be ineffective at physiological concentrations, and the present invention allows for testing under conditions that more nearly represent those found in vivo. The different pH profiles of amyloid self-aggregation (mM concentration of peptide) and deposition (sub-nM concentration of peptide) illustrate the importance of the ability to work at physiological peptide concentrates that is provided by this invention.

EXAMPLE 1

PREPARATION OF LABELLED β-AMYLOID PEPTIDE

A radiolabelled amyloid peptide, $^{125}$I-labelled β-amyloid peptide$^{1-40}$, was synthesized for use in determining binding properties of human β-amyloid peptide tissues in homogenates, and to characterize binding to localize tissue sites with which the peptide interacts in thin sections of normal or Alzheimer's disease tissue including central nervous system and vascular tissue.

Preparation of Peptide

Unlabelled peptides of human β-amyloid peptide$^{1-40}$-OH and β-amyloid peptide$^{25-35}$-OH can be purchased from Bachem, Torrance, Calif., or other vendor. Alternatively, the peptide can be synthesized by solid-phase fluorenylmethoxycarbonyl ("Fmoc") chemistry using techniques described, for example, in J. M. Stewart and J. D. Young, Solid-Phase Peptide Synthesis (2nd edition), pages 74–103 and 147–168, Pierce Chemical Company, Rockford, Ill. (1984); C. M. Deber, Peptides, Structure and Function, pages 221–224 and 249–252, Pierce Chemical Company, Rockford, Ill. (1985); D. H. Schlesinger, Macromolecular Sequencing and Synthesis, Selected Methods and Applications, pages 153–220, Alan R. Liss, Inc., New York (1988); and G. R. Marshall, Peptides, Chemistry and Biology, pages 198–201, ESCOM Science Publishers, Netherlands (1988), the disclosures of which are incorporated by reference herein. It has been shown that the Fmoc strategy offers considerable advantages over the traditional Boc method for preparation of hydrophobic peptides (P. Rovero et al., Int. J. Peptide Protein Res. 37: 140 (1991)). The resin used was polystyrene crosslinked with divinylbenzene and functionalized with an acid-labile linker. Sidechains were blocked with standard acid-labile blocking groups such as BOC, TMOB, and PMC. Alpha-amino groups were blocked with Fmoc. All activations were by diisopropylcarbodiimide and hydroxybenzotriazole in dichloromethane, except Gln and Asn, which were introduced as active (pentafluorophenyl) esters without further activation in dimethylformamide ("DMF") solution. Two-hour couplings were used at each stage of the synthesis. A four-fold molar excess of amino acid monomer over peptide resin was used at each step. Removal of the Fmoc group after each coupling was achieved with 30% piperidine in 1:1 DMF:toluene for 5 and 15 minutes, consecutively. Extensive washings of the resin between chemical steps was with both DMF and DMF:dichloromethane 1:1. Following the final coupling and deblocking cycle, the peptide resin was washed extensively with DMF, DMF:dichloromethane 1:1, and methanol. The peptides were cleaved from the resin using anhydrous trifluoroacetic acid containing 5% thianisole, 3% ethanedithiol, and 2% anisole as scavengers.

The peptides were purified to homogeneity by reverse-phase HPLC using a $C_{18}$-column eluted with a gradient of acetonitrile in 0.01M aqueous TFA according to standard methods, such as those described in J. E. Shively, Methods of Protein Microcharacterization, A Practical Handbook, pages 3–88, Humana Press, Clifton, N.J. (1986), and W. S. Hancock, CRC Handbook of HPLC for the Separation of Amino Acids, Peptides, and Proteins (Vol. II), pages 3–22, 279–286 and 303–312, CRC Press, Inc., Boca Raton, Fla. (1987), the disclosures of which are incorporated by reference herein.

All peptides were further characterized by amino acid analysis and/or peptide sequencing according to standard methods such as those described in Shively supra. Peptides were stored at −20° C. as dry lyophilizates or as stock solutions of $10^{-3}$M concentration in the solvents in which they were purified, i.e., in the HPLC solvents in which they eluted from the $C_{18}$ HPLC column, with 1% 2-mercaptoethanol added as antioxidant. The composition of these solvents varied from 25% to 35% acetonitrile in aqueous 0.01M TFA, with no evidence of peptide oxidation, aggregation or degradation apparent over 4 months. In contrast, storage of the peptides in common solvents used for peptide stock solutions such as water, dimethylsulfoxide, glacial acetic acid, or dimethylformamide gave significant oxidation, aggregation, or degradation resulting in materials not suitable for use in the procedures described below.

Except as otherwise noted, all peptides were based on the human β-amyloid peptide sequence. Accordingly, β-amyloid peptide$^{1-42}$ is H-DAEFRHD-SGYEVHHQKLVFFAEDVGSNKGAIIGLMVGGVVIA-OH [SEQ. ID NO.2]. The analogous peptide in rat and mouse ($G^5$, $F^{10}$, $R^{14}$-β-amyloid peptide$^{1-42}$) differs at three positions within that sequence. Dutch β-amyloid peptide ($Q^{22}$-β-amyloid peptide$^{1-42}$) differs at one position within this sequence. The sequence of β-amyloid peptide$^{25-35}$-NH$_2$ is H-GSNKGAIIGLM-NH$_2$[SEQ. ID NO:3].

Procedure for radioiodination of β-amyloid peptide$^{1-40}$

Peptides containing tyrosine were radiolabelled by oxidative radioiodination using Na$^{125}$I and chloramine-T and separated from free iodide by reverse-phase absorption by modifications described hereinbelow of the methods of W. M. Hunter and F. C. Greenwood, Nature 194: 495 (1962), A. E. Bolton and W. M. Hunter, Biochem. J. 133: 529 (1973), and H.-P. Too and J. E. Maggio, Meth. Neurosci. 6:232 (1991), the disclosures of which are incorporated by reference herein. Peptides not containing tyrosine were first acylated with the N-hydroxysuccinimide ester of 4-hydroxyphenylpropionic acid, and then oxidatively radioiodinated as indicated hereinbelow. Briefly, labelled peptides containing methionine were then reduced from sulfoxide to native form with 2-mercaptoethanol. The iodinated peptides were purified by RP-HPLC to essentially quantitative specific activity (approximately 2000 Ci/mmol) and stored as described hereinabove at a concentration of less than 200,000 dpm/μl.

Acylation with the N-hydroxysuccinimide ester of 4-hydroxyphenylpropionic acid followed the method of H.-P. Too and J. E. Maggio, Meth. Neurosci. 6: 232 (1991), the disclosure of which is incorporated by reference herein. Care was taken to purify for future labelling only the monoacyl derivatives of the peptides, which were recognized by their elution profiles.

Standard radioiodination procedures such as those described in W. M. Hunter and F. C. Greenwood, supra, A. E. Bolton and W. M. Hunter, supra, and H.-P. Too and J. E. Maggio, supra, do not yield a viable tracer. It was found that iodination of the peptide must be performed at high buffer concentration (0.5M sodium phosphate, pH 7.5). However, since under those conditions solutions of the peptide are substantially unstable, it is necessary to perform the iodination step quickly. Preferably, the labelling reaction from the point of dissolving the dry peptide in the phosphate buffer to loading the reaction mixture onto an octyldecylsilica cartridge is completed within about one minute. If this part of the procedure is not completed in a sufficiently short period of time, the β-amyloid peptide will aggregate and fail to yield useful tracer.

It was found that successful iodination of the β-amyloid peptide requires starting with the peptide in its dry (lyophilized) form. It was found that peptide placed in typical solvents such as aqueous buffer or dimethylsulfoxide did not yield a viable tracer. It was further found that the peptide remains stable in the solvent in which it is purified (35% acetonitrile in 0.01M aqueous TFA). Thus, the peptide (10 nmol) is loaded into the reaction vessel (a polypropylene microcentrifuge tube) by placing an aliquot of peptide solution in this solvent in the reaction vessel and then stripping the solvent in a vacuum centrifuge. It is preferred that a high molar ratio of peptide to radioiodine is used to minimize diiodination since the monoiodinated form is preferred for use in the assays described herein.

It was found that the labelled peptide is viable as a tracer only when in the reduced (native methionine sidechain) form at high specific activity. Therefore, additional steps of reduction and purification to high specific activity are necessary after the labelling reaction and its workup. Typical radioiodination syntheses are halted after labelling and the products used without additional steps. Such products, consisting of low specific activity peptides containing oxidized methionine, are acceptable for the majority of applications of peptide tracers such as radioimmunoassay. It was found that production of viable β-amyloid peptide tracer requires the additional steps of reduction and purification as described hereinbelow.

It was determined that in order to avoid aggregation of the labelled peptide and consequent loss of viable tracer during the reduction reaction, the reaction time must be 90 minutes or less. Although reduction of the sulfoxide form is not complete at 90 minutes, the labelled β-amyloid peptide remains mostly as intact monomer. Longer reaction times provide complete reduction at the risk of formation of unusable aggregates.

The purification of the monoiodinated reduced tracer is accomplished by reverse-phase HPLC using a shallow gradient of acetonitrile in aqueous 0.01M TFA which is capable of resolving oxidized from reduced forms, and uniodinated from monoiodinated from diiodinated forms of the β-amyloid peptide. It is preferred that the reduced monoiodinated form of the peptide is used in the assays described below.

To 10 nmol of dry β-amyloid peptide$^{1-40}$ in a polypropylene microcentrifuge tube is added 40 µl of 0.5M sodium phosphate pH 7.5 and 10 µl (=1 mCi) of aqueous Na$^{125}$I, and the tube is vortexed briefly. Chloramine-T (10 µl of 1 mg/ml in distilled water, freshly dissolved) is added to the mixture and the tube vigorously vortexed for 15 to 30 seconds. The reaction is then terminated by the addition of Na$_2$S$_2$O$_5$ (20 µl of 10 mg/ml in distilled water), followed by brief vortexing.

The reaction mixture is immediately loaded onto an octyldecylsilica cartridge (volume approximately 0.5 ml) previously primed by washing with 3 ml acetonitrile containing 0.01M TFA followed by 3 ml 0.01M aqueous TFA. Examples of suitable octyldecylsilica cartridges include C$_{18}$ SPICE (Analtech), C$_{18}$ spe (Baker), and C$_{18}$ Sep-Pak (Waters). The octyldecylsilica cartridge is then eluted in step gradient fashion successively with 0.5 ml each of 0.01M aqueous TFA containing 10%, 20%, and 40% alcohol, and then eluted with 1 ml each of 80% and 100% alcohol, where alcohol is methanol:ethanol in a 1:1 volume. The labelled peptide of interest elutes in the 80% alcohol fraction. During elution of the cartridge, it is preferred that a slow flow rate is used, that air bubbles are avoided, and that the cartridge not be allowed to dry out to avoid adverse effects on the yield of labelled peptide.

The labelled peptide fraction which elutes from the octyldecylsilica cartridge includes the oxides of unlabelled, monoiodinated, and diiodinated peptides in alcoholic aqueous 0.01M TFA. Chemical reduction to the native methionine forms is accomplished by concentrating the solution to less than about 25% of its original volume by gently evaporating the alcohol in a nitrogen stream, then adding neat 2-mercaptoethanol to a final concentration of 20%, and heating the resulting solution in a tightly capped tube under nitrogen at 90° C. for 90 minutes. After cooling to room temperature, the mixture is purified by reverse-phase HPLC as described above, and the appropriate radioactive peptide (the reduced, monoiodinated form) retained for future use. Immediately following purification, 1% 2-mercaptoethanol is added to the purified tracer to prevent oxidation to the useless sulfoxide form. The tracer now preferably at 2000 Ci/mmol (for $^{125}$I), is stored as indicated above. At –20° C., solutions of less than 200,000 dpm/µl are stable for at least 4 months.

EXAMPLE 2

DETECTION OF IN VITRO β-AMYLOID PEPTIDE DEPOSITION IN HUMAN TISSUE AND USE OF LABELLED β-AMYLOID PEPTIDE

Preparation of tissue homogenates and thin sections

Brain tissue was obtained form normal and Alzheimer's disease patients at 0.5 to 14 hours postmortem, frozen on dry ice after collection, and stored at –20° C. until use. For filter binding studies, tissue homogenates were prepared after the method of H. P. Too and M. R. Hanley, *Biochem. J.* 252:545 (1988), the disclosure of which is incorporated by reference herein. Tissue was homogenized (Polytron, setting 7–8, 5–10 sec) in 5–10 volumes of 50 mM Tricine (pH 7.5) containing 10% sucrose and protease inhibitors (0.01% bacitracin, 0.002% soybean trypsin inhibitor, 0.0002% chicken egg trypsin inhibitor, 1 mM benzamidine hydrochloride) and pelleted at 10,000 g for 20 minutes. The homogenate was then resuspended and washed several times in Tricine buffer containing 120 mM NaCl, 10 mM EDTA, 300 mM KCl and centrifuged at 40,000 g for 20 minutes and stored at –20° C. for less than two months. Membranes (equivalent to about 30 mg tissue) were resuspended in 0.5 ml 50 mM TrisHCl (pH 7.5) containing 1 mg/ml bovine serum albumin (BSA), 10 mM MnCl$_2$, 0.004% bacitracin, 0.002% chymostatin, 0.004% leupeptin, 0.1% dimethylsulfoxide for 30 minutes prior to addition of the radioligand ($10^{-11}$ to $10^{-9}$M) and various concentrations of unlabelled peptides in the same buffer.

After incubating for two hours at room temperature, the homogenates (final volume 0.575 ml) were filtered through glass fiber filters (Whatman GF/D), presoaked for at least two hours in 1 mg/ml BSA and rinsed with 25 mM Tricine (pH 7.5). After washing twice with 25 mM TrisHCl (pH 7.5) at room temperature, the filters were counted in a gamma counter. Signal/noise and specific binding were a function of the density of plaques in the tissue.

In Alzheimer's disease tissue homogenates, about 20,000 cpm (20%) of the $^{125}$I-labelled β-amyloid peptide$^{1-40}$ was bound in the absence of unlabelled peptides, and 10000 cpm (10%) in the presence of $10^{-5}$M unlabelled β-amyloid peptide$^{1-40}$. No displacement binding was observed when plaques were absent (i.e., in normal tissue). Autoradiography of the homogenate confirmed that the highest density of binding sites in Alzheimer's disease tissue was on intact plaques.

Autoradiography

For tissue autoradiography, unfixed tissue was serially sectioned at 5–15 μm and thaw-mounted onto gelatin-coated slices. Slide-mounted sections were stored at −20° C. in closed boxes over desiccant for less than three months before use. Sections were preincubated for 30 minutes and incubated with the radioligand for two hours under the same conditions according to the aforedescribed homogenate binding study. Alternatively, 50 mM TrisHCl rather than Tricine may be used as the buffer. For estimating nonspecific binding, paired serial sections were incubated with the radioligand in the presence of a $10^4$ to $10^5$ fold excess of the unlabelled peptide. Following incubation with the radioligand, the slides were washed with 50 mM TrisHCl pH 7.5 (four times, two minutes each at 4° C.), then dried at 4° C. and stored in closed boxes over desiccant at room temperature overnight. The fully dried slides were then placed in apposition to tritium-sensitive film alongside iodinated standards. After one week's exposure at −20° C., the film was developed, fixed and washed. Sections were later dipped in photographic emulsion for higher resolution autoradiography and/or counterstained by standard procedures with Congo red, thioflavin S, creosyl violet, hematoxylin and eosin, or antibodies for immunohistochemical analysis. This approach generated film autoradiograms for quantitative densitometry, a high resolution emulsion autoradiograms for detailed histology, and a counterstained section for identification of cell types from each tissue section.

RESULTS

While there was essentially no displaceable binding of the radioligand to normal tissue homogenates or sections, there was significant displaceable binding to Alzheimer's disease tissue (see FIGS. 1 and 2). The binding to Alzheimer's disease tissue was not saturable, suggesting that most of the sites to which the radioligand bound were not receptors in the usual sense (i.e., receptor directly coupled to an effector mechanism that directly affects the intra-cellular environment). Rather, the characteristics of this binding were consistent with growth of Alzheimer's disease amyloid plaques by deposition of β-amyloid peptide from solution.

Radiolabelled human β-amyloid peptide was deposited in vitro from dilute ($10^{-11}$–$10^{-9}$M) solution onto neuritic, diffuse, and cerebrovascular plaques in AD brain tissue, within 30 to 60 minutes. These dilute concentrations of β-amyloid peptide correspond to those subnanomolar (<$10^{-9}$) concentrations of β-amyloid peptide found physiologically. In tissue without preformed plaques, no deposition was detected. These results indicate that all three types of plaques are capable of growth through deposition of exogenous amyloid peptide in the presence of very low amounts (i.e., those levels found physiologically) of β-amyloid peptide. These results further indicate that plaque growth alone does not explain the selective damage to particular subsets of neurons which typifies the disease process.

Visualization of the binding sites for $^{125}$I-β-amyloid peptide$^{1-40}$ by autoradiography showed that the ligand was deposited on amyloid plaques at both parenchymal and vascular sites in Alzheimer's disease brain. Thus, in the Alzheimer's disease cerebral cortex, $^{125}$I-β-amyloid peptide$^{1-40}$ was deposited on both the core and the halo of essentially every extracellular plaque examined (FIG. 2). In the Alzheimer's disease cerebellar cortex, diffuse plaques which were not visualized with thioflavin S were readily labelled with the β-amyloid peptide radioligand (see FIG. 2), and clear morphological differences between these plaques and the compact plaques of the cerebral cortex were evident. Thus, both the classic senile plaques of the cortex and the diffuse nonneuritic deposits of the cerebellum were found capable of in vitro growth by addition of β-amyloid peptide from dilute solution. While thioflavin S and anti-A4 antibodies stained neurons outside the plaques as well as the plaques themselves, deposition of the radioligand was limited to the plaques alone (see FIG. 2). Furthermore, the sensitivity of detection of plaques with the radioligand far exceeded that of dyes or antibodies. Thus, the radioligand was capable of detecting more lesions at a potentially earlier time than detection techniques reported to date. In cerebral cortex tissue obtained from normal brain, there was essentially no deposition of β-amyloid peptide radioligand detected above background levels at parenchymal or vascular sites.

Vascular plaques were visualized by β-amyloid peptide deposition in approximately 0–20% of intra- and extraparenchymal blood vessels in Alzheimer's disease brain, although the fraction of vessels labelled showed considerable variation between cortical areas examined and between patients (see Table II). The cerebrovascular deposits were consistently labelled more densely than cerebral plaques within the same section. In vessels seen in transverse section (see FIG. 6), the deposition of β-amyloid peptide radioligand was not uniform but concentrated in a part of the vessel, apparently the tunica media. Endothelial tissue was not labelled.

Deposition of $^{125}$I-β-amyloid peptide$^{1-40}$ onto plaques in both homogenates and sections of Alzheimer's disease tissue was significantly attenuated by excess unlabelled β-amyloid peptide$^{1-40}$ and Dutch β-amyloid peptide$^{1-40}$, as addition of these unlabelled peptides to the plaques competed with deposition of the radioligand (see FIG. 4). β-amyloid peptide$^{25-35}$-NH$_2$ also competed with the 40-mer radioligand when the former was present at much higher concentrations (see FIG. 4), while the free acid β-amyloid peptide$^{25-35}$-OH had no detectable activity in the assay. Thus, the growth of amyloid plaques in vitro required only the presence of β-amyloid peptide in the surrounding media. The affinity of the amyloid peptide for the plaques was sufficiently high that even when the concentration of β-amyloid peptide$^{1-40}$ was below $10^{-11}$M (below physiological levels), deposition occurred. No significant differences in β-amyloid peptide deposition were noted between homogenates and sections of Alzheimer's tissue nor were any significant differences noted between Alzheimer's disease cerebral cortex (neuritic plaques) and cerebellum (diffuse plaques). These results were consistent with the hypothesis that the plaques themselves (neuritic, diffuse, and vascular) can grow in vivo in the presence of β-amyloid peptide.

Figure 4:
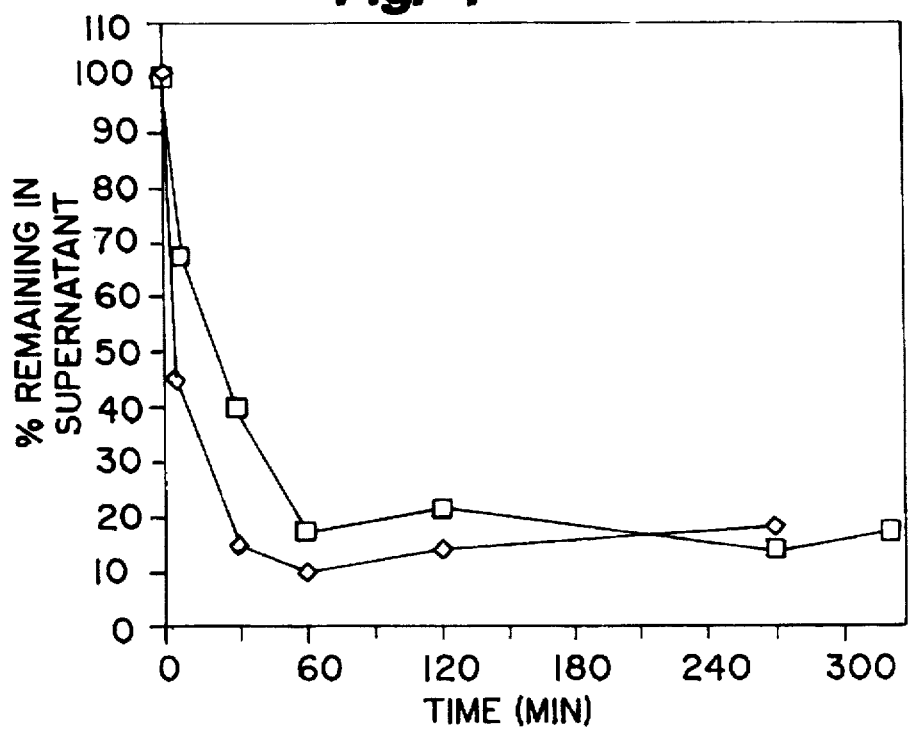
FIG. 4 is a graphic depiction of in vitro aggregation of ↑ human $^{125}$I-β-amyloid peptide$^{1-40}$ ($^{125}$I-βA(1–40)-OH), and ◊ human $^{125}$I-β-amyloid peptide$^{1-40}$ ($^{125}$I-βA(1–40)-OH) in the presence of sodium dodecylsulfate (SDS).

The mammalian tachykinins, substance P and neurokinins A and B, over a broad range of concentration, did not inhibit the deposition of radiolabelled β-amyloid peptide onto Alzheimer's disease plaques (see FIG. 4). Binding sites for radiolabelled tachykinins were present in both Alzheimer's disease and normal tissue, and were not associated with plaques. These tachykinin binding sites were indistinguishable from the tachykinin receptors that have been described by J. E. Maggio, *Ann. Rev. Neurosc.*, 11: 13 (1988), and P. W. Mantyh et al., *Proc. Natl. Acad. Sci.*, 86: 5193 (1989), with unlabelled tachykinins displacing their radiolabelled analogues at nanomolar concentrations. In contrast, there was no displacement of any of the tachykinin radioligands by β-amyloid peptide$^{1-40}$ at concentrations up to 30 μM, which indicates that the amyloid peptides not interact with tachykinin receptors under the standard conditions labelling tachykinin receptors as described. These results were consistent with the reported structure-activity studies among the tachykinin peptide family, namely, that a carboxyl-terminal amide is required for activity.

Radiolabelled rat β-amyloid peptide$^{1-40}$ failed to bind to Alzheimer's disease or normal human tissue, or to adult rat brain. In addition, unlabelled rat β-amyloid peptide$^{1-40}$ did not inhibit deposition of $^{125}$I-β-amyloid peptide$^{1-40}$ onto Alzheimer's disease plaques. These results are consistent with the observation that rodents do not develop amyloid plaques, and indicates that the sequence of the amyloid peptide itself is important in plaque genesis and growth.

The avidity of β-amyloid peptide for amyloid plaques indicates that once an aggregate of amyloid peptide has formed, even extremely low concentrations of β-amyloid peptide will support its growth. It was found that neuritic, diffuse, and vascular plaques were indistinguishable in this capacity. Since neuritic plaques in the cerebral cortex were often surrounded by dying neurons while diffuse plaques in the cerebellum were not, these results indicate that if β-amyloid peptide is neurotoxic, it is selectively neurotoxic to a subset of central neurons.

The use of radioiodinated β-amyloid peptide provides an in vitro system for the quantitative evaluation of agents or conditions which may inhibit or enhance the growth of plaques under physiological conditions, a sensitive method for visualizing various types of amyloid deposits, a means for characterizing and locating sites of amyloid peptide binding to cells and tissues, and for investigation of the role of amyloid deposits in the pathogenesis of Alzheimer's disease.

EXAMPLE 3

IN VITRO EVALUATION OF AGENTS FOR INHIBITING OR ENHANCING AGGREGATION OF β-AMYLOID PEPTIDE, OR FOR DISPERSING AGGREGATES OF β-AMYLOID PEPTIDE, IN THE ABSENCE OF ALZHEIMER'S DISEASE PLAQUES

The experiments described in Example 1 demonstrated that amyloid plaques can grow in vitro by deposition of labelled amyloid peptide from dilute solution. The following experiment with radiolabelled β-amyloid peptide demonstrated that the peptide can aggregate in vitro in the absence of amyloid plaques. This latter property provides an in vitro system for qualitative and quantitative evaluation of agents or conditions that may inhibit or enhance this aggregation or disperse preformed aggregates. Agents so identified may have similar effects on Alzheimer's disease plaques in vivo.

A solution of about $10^{-9}$M labelled β-amyloid peptide in 50 mM Tricine buffer at pH 7.5 was prepared from stock solution of the peptide as described hereinabove in Example 1. The solution was aliquotted into several reaction vessels (polypropylene microcentrifuge tubes) and allowed to stand at room temperature with occasional vortex mixing. At various times, the tubes were centrifuged at 12000 g for 4 minutes, and the fraction of initial (t=0) cpm of labelled peptide remaining in the supernatant fraction determined by removing a small aliquot for counting. The time course of the disappearance of the tracer from the supernatant under these conditions is shown in FIG. 4. The rate of disappearance was dependent on a variety of other conditions which were evaluated using this assay. Thus, the rate of the disappearance depends on peptide concentration (faster at higher peptide concentrations), and on ionic strength (faster at higher salt concentrations). The rate of disappearance was further dependent on the presence of certain detergents such as sodium dodecylsulfate (SDS) (faster in 0.01% SDS; see, FIG. 4), and on the presence of certain organic solvents (slower in the presence of acetonitrile).

Methods similar to those described hereinabove may be used to assay the rate of formation of aggregates which may be separated by filtration or centrifugation, or the rate of dispersion of aggregates of amyloid peptide, or the effects of various agents on these processes. In each case, a key step is the use of labelled amyloid peptide in the aggregation or in solution to follow the time course of the process.

EXAMPLE 4

IN VITRO EVALUATION OF AGENTS FOR INHIBITING OR ENHANCING PLAQUE GROWTH

The competitive binding assay, as described in FIG. 4, was conducted to determine inhibition of $^{125}$I-β-amyloid peptide$^{1-40}$ aggregation by amyloid and tachykinin peptides in homogenates of Alzheimer's disease temporal cortex. The aggregation affecting agents that were tested included β-amyloid peptide$^{1-40}$, β-amyloid peptide$^{25-35}$-NH$_2$, β-amyloid peptide$^{25-35}$-OH, rat β-amyloid peptide$^{1-40}$, substance P, and neurokinins A and B.

As shown in Table II, patients considered to have Alzheimer's disease were clinically diagnosed as such, and contained numerous plaques, as determined by thioflavin S staining of brain tissue samples. Control subjects were age-matched patients with no history of dementia.

Tissue homogenates of temporal cortex tissue obtained from the control subjects were prepared according to the protocol set forth in Example 1. Autoradiography, also as set forth in Example 1, indicated the absence of amyloid plaques in the homogenized tissue material. (See, Table II). As the tissue samples displayed no evidence of Alzheimer's disease, the samples were considered "normal" tissue, and used as controls.

Tissue homogenates of temporal cortex tissue obtained from patients with Alzheimer's disease were also prepared according to Example 1 (See, Table II). Autoradiography detected amyloid plaques in the homogenized tissue material.

Inhibition of $^{125}$I-β-amyloid peptide$^{1-40}$ deposition was determined by adding increasing concentrations of the deposition affecting agents/peptides to the incubation medium and determining the percent inhibition of deposition. FIG. 4 shows that whereas β-amyloid peptide$^{1-40}$ or Dutch β-amyloid peptide$^{1-40}$ are potent inhibitors of $^{125}$I-β-amyloid peptide$^{1-40}$ deposition, β-amyloid peptide$^{25-35}$-NH$_2$ is substantially less potent and substance P, Neurokinin A and B, β-amyloid peptide$^{25-35}$-OH, and rat β-amyloid peptide$^{1-40}$ are essentially inactive. This shows the usefulness of this assay in assessing an agent's ability to inhibit β-amyloid peptide$^{1-40}$ deposition to pre-formed plaques.

EXAMPLE 5

LOCALIZATION OF $^{125}$I-β-AMYLOID PEPTIDE$^{1-40}$ BINDING SITES IN ALZHEIMER'S DISEASE BRAIN TISSUE

Tissue sections of Alzheimer's disease temporal cortex from Example 3 were examined by autoradiography to detect binding sites of $^{125}$I-β-amyloid peptide$^{1-40}$.

There was no specific deposition of β-amyloid peptide$^{1-40}$ in the absence of plaques. As shown in FIG. 2, an autoradiograph of $^{125}$I-β-amyloid peptide$^{1-40}$ binding in tissue sections of Alzheimer's disease temporal cortex, tissue from areas without plaques showed no binding of $^{125}$I-β-amyloid peptide$^{1-40}$ which could be displaced by excess β-amyloid peptide$^{1-40}$.

Figure 2B:
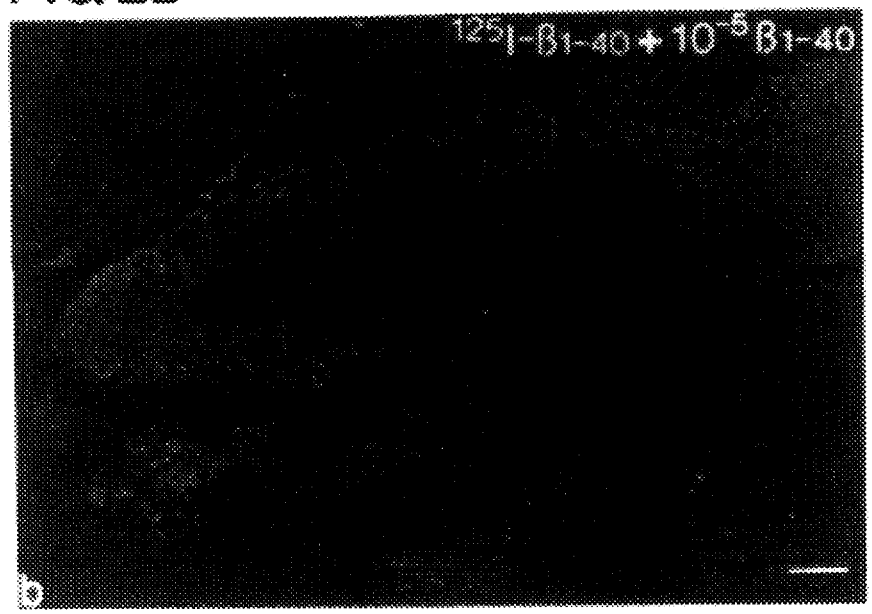
Figure 2C:
Figure 2D:
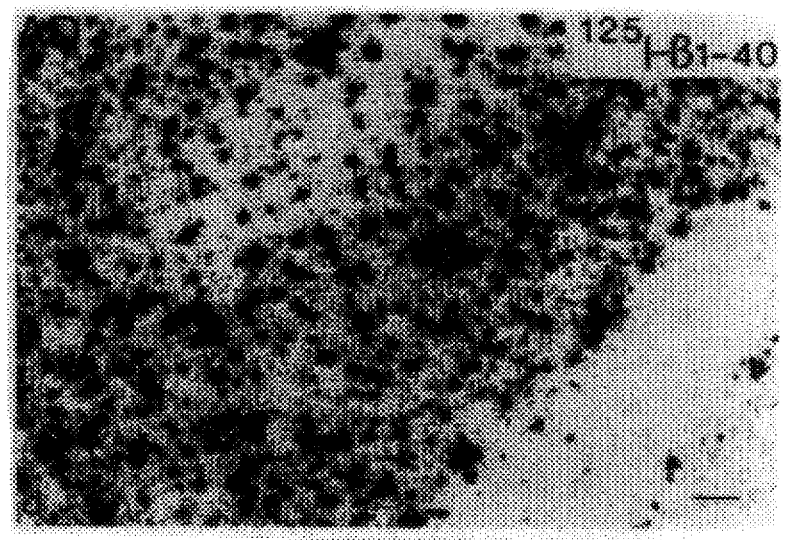
Figure 2E:
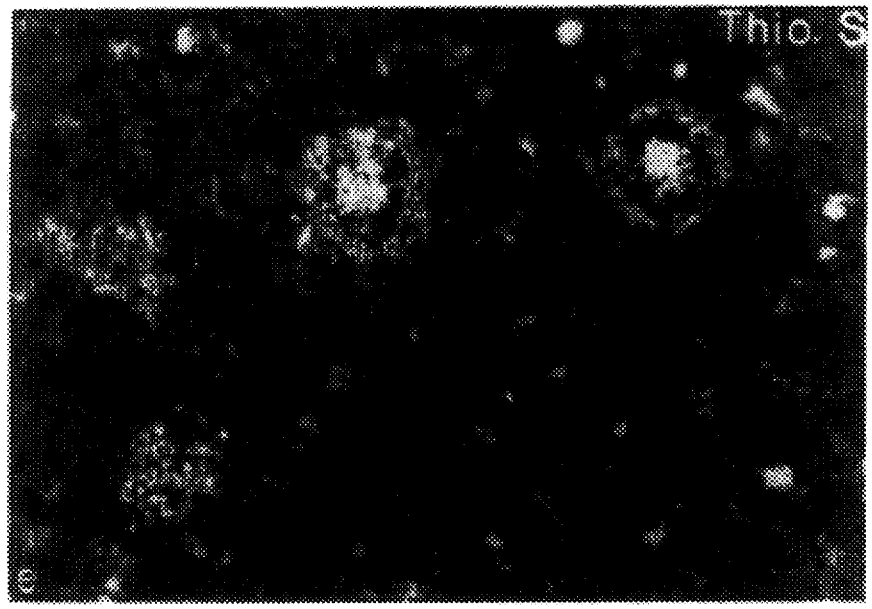
Figure 2F:
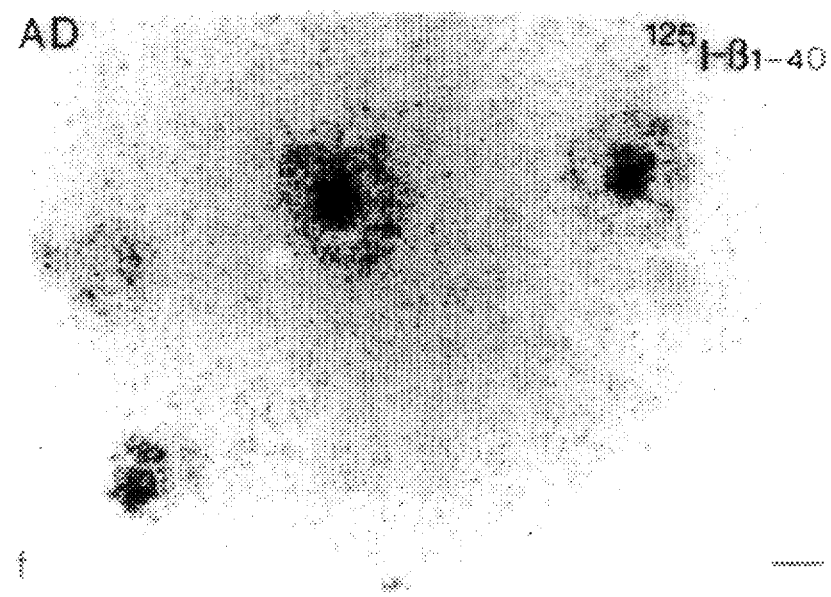
Figure 2G:
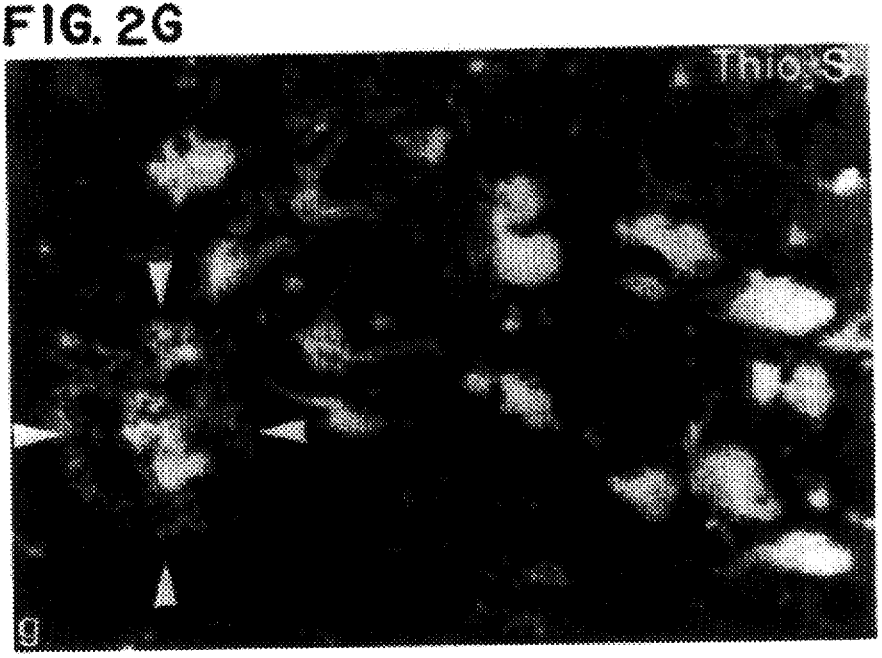
Figure 2H:
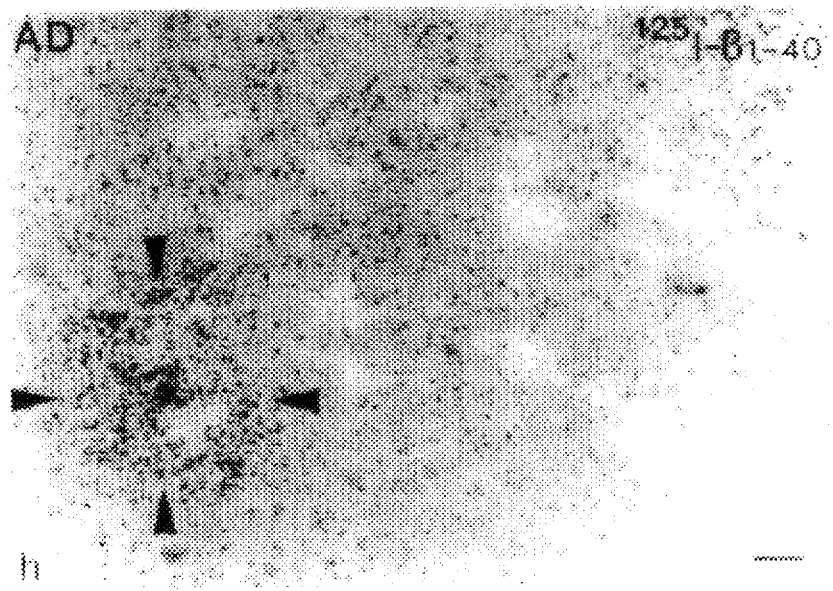
Figure 3A:
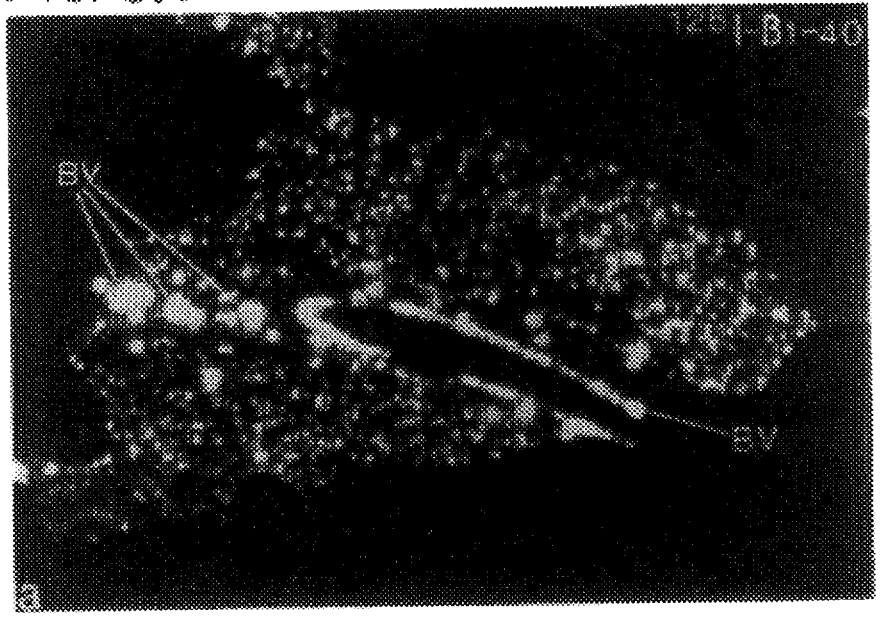
FIG. 3a–3d are an autoradiographic localization of $^{125}$I-β-amyloid peptide$^{1-40}$ ($^{125}$I-βA(1–40)-OH) binding sites in the parenchyma and cerebral vasculature of Alzheimer's disease brain tissue.
Figure 3B:
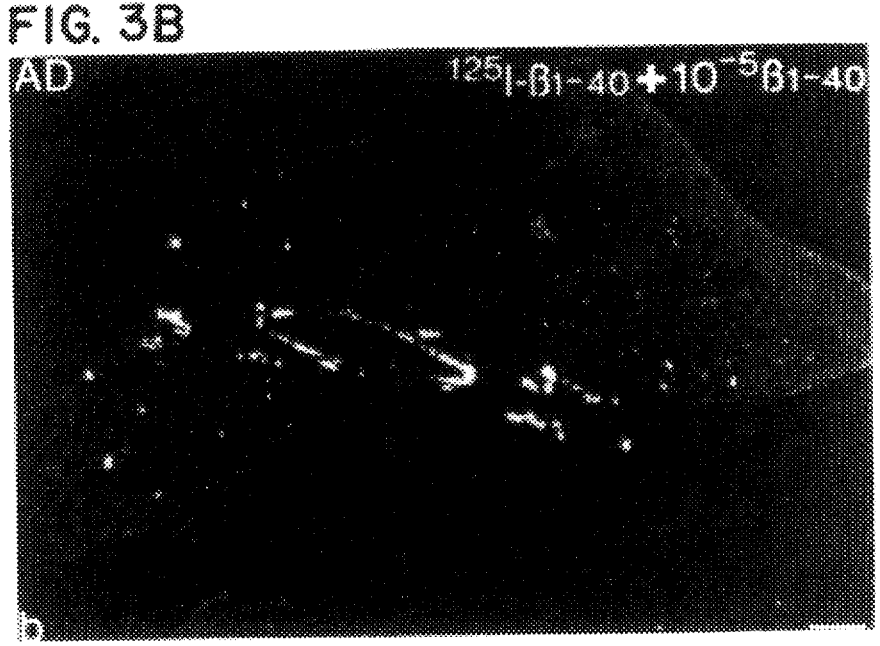
Figure 3C:
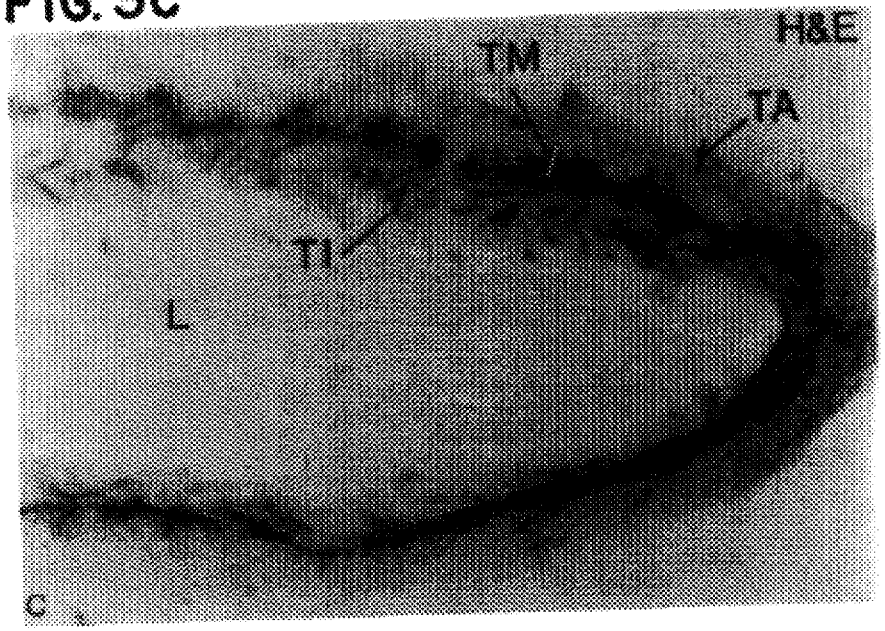
Figure 3D:
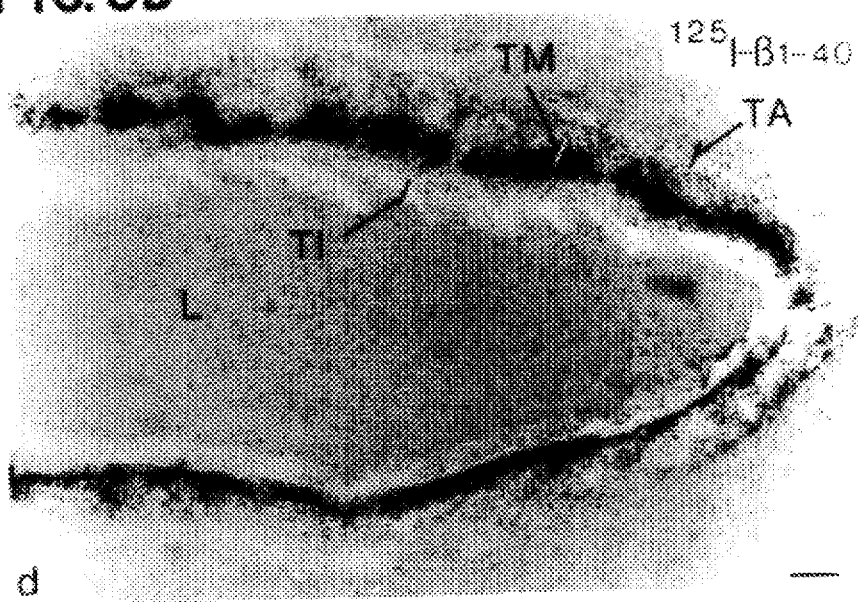

A dark field photomicrograph showing the distribution of $^{125}$I-β-amyloid peptide$^{1-40}$ in Alzheimer's disease temporal cortex revealed numerous plaques throughout the grey matter (FIG. 2(a)). A dark-field micrograph of a serially adjacent section as treated in FIG. 2(a), except that $10^{-5}$M cold β$_{1-40}$ was added to the incubation medium, is shown in FIG. 2(b). An immunohistochemistry of amyloid deposits using antibodies raised against β-amyloid peptide$^{1-40}$ (amyloid peptide A4) in Alzheimer's disease temporal cortex is shown in FIG. 2(c). FIG. 2(d) is a dark-field photomicrograph of the same section as shown in FIG. 2(c), where $^{125}$I-β-amyloid peptide$^{1-40}$ revealed a more extensive distribution of plaques than did the anti-A4 antibody. FIG. 2(e) is a dark-field photomicrograph of thioflavin S staining in human Alzheimer's disease temporal cortex showing labelling of diffuse, compact and neuritic type plaques. FIG. 2(f) is a light-field photomicrograph of the same section as FIG. 2(e) bound with $^{125}$I-β-amyloid peptide$^{1-40}$, showing that all three types of plaques bind $^{125}$I-β-amyloid peptide$^{1-40}$. FIG. 2(g) is a dark-field photomicrograph of thioflavin S staining in human Alzheimer's disease temporal cortex showing labelling of a neuritic plaque and several adjacent neurons. FIG. 2(f) is a light-field photomicrograph showing the same section as FIG. 2(g), bound with $^{125}$I-β-amyloid peptide$^{1-40}$, showing that although both the core and halo of the plaque bind $^{125}$I-β-amyloid peptide$^{1-40}$, none of the labelled neurons show any $^{125}$I-β-amyloid peptide binding.

Localization of $^{125}$I-β-amyloid peptide$^{1-40}$ binding sites in the cerebral vasculature of Alzheimer's disease brain is shown in FIG. 3. FIG. 3(a) shows the distribution of $^{125}$I-β-amyloid peptide$^{1-40}$ in plaques in the parenchyma and in blood vessels (BV) in Alzheimer's disease temporal cortex. FIG. 3(b) shows a serially adjacent section treated in the same way as that of FIG. 3(a), except that $5.0\times10^{-5}$M cold β-amyloid peptide$^{1-40}$ was added in the incubation medium. FIG. 3(c) is a light-field photomicrograph showing the localization of $^{125}$I-β-amyloid peptide$^{1-40}$ in a cerebral artery. FIG. 3(d) is a dark-field photomicrograph of the same section as in FIG. 3(c) showing the binding of $^{125}$I-β-amyloid peptide over the tunica media of the cerebral artery.

EXAMPLE 6

UTILIZATION OF SILK IN PLACE OF HUMAN ALZHEIMER'S DISEASE PLAQUES IN THE IN VITRO EVALUATION OF AGENTS FOR INHIBITING OR ENHANCING PLAQUE GROWTH

Materials

Spider silk was obtained from draglines spun by three ordinary species of spiders captured in the inventors' laboratory. Only one of the species was positively identified, *Nephila clavipes*. Insect silk (Bombyx silkworm silk) was obtained from fabric shops. Commercially available silk fabrics including natural tan pongee, doupioni cloth, and undyed ceilan katia yarn were obtained from Thai Silks, 252 State St., Los Acros, Cailf. 94022. Control fabrics such as nylon and cotton were also obtained commercially. Most experiments were done with undyed ceilan katia yarn because it is easy to work with and can be purchased from any local yarn shop. All other reagents were obtained as described in Example 2.

Methods.

Labelled β-amyloid peptide [$^{125}$I-βA(1–40)-OH] was prepared as described in Example 1. Peptide deposition was conducted and detected as described in Example 2, except that instead of using brain tissue obtained from patients with Alzheimer's disease, silk was used as a template for β-amyloid deposition. The silk specimens were wound about or placed on a glass microscope slide and treated exactly as a piece of Alzheimer's disease (AD) brain tissue was treated in Example 2, using the same solutions, incubations times, etc. Experiments involving AD brain sections and control fabrics, such as nylon and cotton, were conducted in parallel.

In an initial experiment, two each of 6 cm sections of silk, nylon and cotton thread were cut and placed in individual tubes each containing 1 mL of 100 mM Borate RIA buffer, pH 8.5, plus 0.1% Tween-80. After two hours of incubation at room temperature, threads were transferred to new tubes each containing 1 mL of $^{125}$I-βA(1–40)-OH tracer in 100 mM Borate buffer plus 0.1% Tween-80. Threads incubated at room temperature for eight days, then supernatant was removed and saved individually. 50 μL samples of each supernatant was taken for counting. Threads were rinsed twice in 100 mM Borate buffer, pH 8.5, and counted. After counting, each individual supernatant was returned to its thread and the threads were incubated for seven days at 37° C. At the end of seven days, 50 μL samples of each supernatant were taken for counting, threads were rinsed twice in 100 mM Borate buffer, pH 8.5, and counted. The supernatant was again returned to its individual thread, and threads were incubated for another seven days at 37° C. This procedure was repeated once more for a total of 21 days incubation at 37° C. in addition to the eight days incubation at room temperature. After 21 days incubation at 37° C., 50 μL samples were taken from each supernatant, threads were rinsed twice in 100 mM Borate buffer, pH 8.5, and counted. Threads were then rinsed quickly in 1 mL each of distilled water, recounted, and dried on filter paper. Dried threads were tacked to the filter paper, and placed in a cassette with XOmat film and an intensifying screen for 2 weeks exposure at −20° C. Results are reported in Table 3 and FIG. 8.

Deposition of $^{125}$I-βA(1–40)-OH onto ceilan katia yarn, raw silk (provided by S. Santikarn, Bangkok) and silks 15G (organza sheer stiff silk, Thai Silks), 22R (natural tan pongee, Thai Silks) and 16F (silk doupioni, Thai Silks) was tested under similar conditions, except that the buffer contained 0.2% bovine serum albumin (BSA). $^{125}$I-βA(1–40)-OH tracer was used in a concentration of 30 pM. Results are shown in Table 4.

Although screens of the many available silks were done at pH 8.5, later experiments were conducted at a preferably lower pH. Silk deposition experiments were done in 96-well plates. Labelled β-amyloid peptide concentration ranged from 20–100 pM, and the amount of silk used per assay ranged 0.5 to 5 mg.

The kinetics of binding activity were examined using varying concentrations of $^{125}$I-βA(1–40)-OH in the deposition assay described in Example 2 except that in place of AD tissue, ceilan katia yarn (0.5 mg per reaction) was used. The amount of $^{125}$I-βA(1–40)-OH tracer in the reaction mixture ranged from 0 to 600 pmol.

pH dependence of deposition was similarly examined using the deposition assay described in Example 2.

The impact of detergents on the deposition rate of $^{125}$I-βA(1–40)-OH tracer onto silk was also examined. Detergent concentration was varied from 0 to 1%. Detergents tested were Zwittergent 312 (Calbiochem, San Diego, Cailf.) (zwitterionic detergent), Triton-X 100 (a nonionic detergent, Sigma Chemical Company, St. Louis, Mo.), and sodium dodecyl sulfate (an ionic detergent, Sigma Chemical Company, St. Louis, Mo.).

Results

Figure 8:
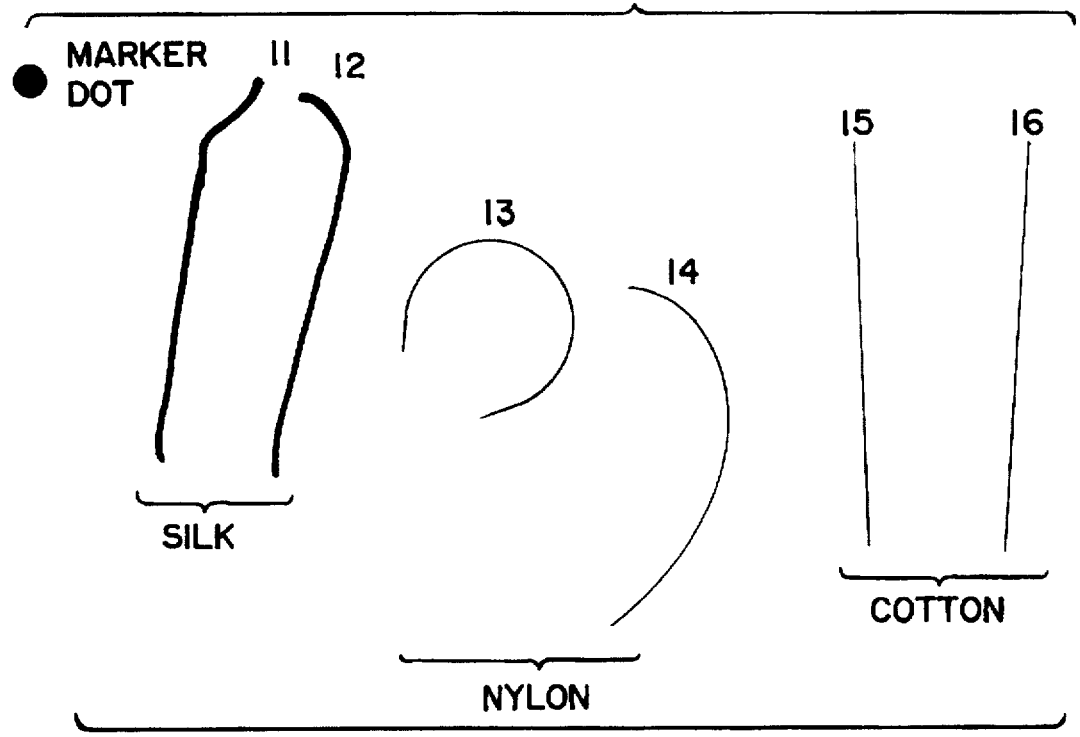
FIG. 8 is an autoradiogram of $^{125}$I-βA(1–40)-OH deposition onto silk, nylon and cotton as described in Example 6. See also Table 3.

Table 3 shows the results of $^{125}$I-βA(1–40)-OH tracer deposition on silk, nylon and cotton. For silk, the average cpm observed after 21 days of incubation at 37° is 2626, whereas cotton and nylon averaged 108 and 236 cpm, respectively. Table 4 compares a number of different commercially available silks. Tracer deposition occurred on all tested silks, ranging from 60 to 253 cpm per hour per mg silk. Celian katia yarn, used for subsequent experiments, exhibited 153 cpm per hour per mg silk. Other silks have also been tested, and all promote deposition of tracer peptide. Autoradiograms of the threads are shown in FIG. 8.

TABLE 3

| Sample Material | Number | 8 Days at Room Temp. | 7 Days at 37° C. | 14 Days at 37° C. | 21 Days at 37° C. | Distilled Water rinsed 21 day thread |
|---|---|---|---|---|---|---|
| SILK | 1 | 1051.6 | 1831.2 | 2328.0 | 2928.6 | 2839.4 |
|  | 2 | 1089.6 | 1626.2 | 1978.0 | 2322.6 | 2315.4 |
|  | average | 1070.6 | 1728.7 | 153.20 | 2625.6 | 2577.4 |
| NYLON | 1 | 161.6 | 189.2 | 252.0 | 265.6 | 205.4 |
|  | 2 | 169.6 | 175.2 | 180.0 | 205.6 | 189.4 |
|  | average | 165.6 | 182.2 | 216.0 | 235.6 | 197.4 |
| COTTON | 1 | 282.2 | 128.7 | 158.7 | 126.4 | 108.0 |
|  | 2 | 239.7 | 176.3 | 105.1 | 90.0 | 102.0 |
|  | average | 261.0 | 152.5 | 131.9 | 108.2 | 105.0 |

TABLE 4

| SILK TYPE | ON-RATE[2] |
|---|---|
| Ceilan Katia Yarn | 153 ± 8 (4) |
| Raw Silk[3] | 47 ± 2.5 (3) |
| Organza Sheer Stiff Silk (15G)[4] | 60.6 (1) |
| Natural Tan Pongee 22R[4] | 253 (1) |
| Silk doupioni 16F[4] | 245 (1) |

[1]Buffer was 0.1M sodium borate, 0.1% Tween-80, 0.2% Bovine serum albumin (BSA), pH 8.5. Reactions were conducted at 37° C. using 30 pM radiolabelled tracer.
[2]The on-rate is expressed in cpm $^{125}$I/hour/mg silk. The values represent mean ± SEM. The number in parentheses is n, the number of samples tested.
[3]From S. Santikarn (Bangkok).
[4]Obtained from Thai Silks, 252 State St., Los Acros, CA 94022.

First order binding kinetics (a linear relationship between tracer amounts and binding) for ceilan katia yarn (6 cm and 2 cm lengths) were confirmed. Previous research by others into the kinetics of plaque deposition onto AD tissue have suggested higher order kinetics, however those results were obtained at higher (µM), nonphysiological concentrations of amyloid peptide.

Figure 9:
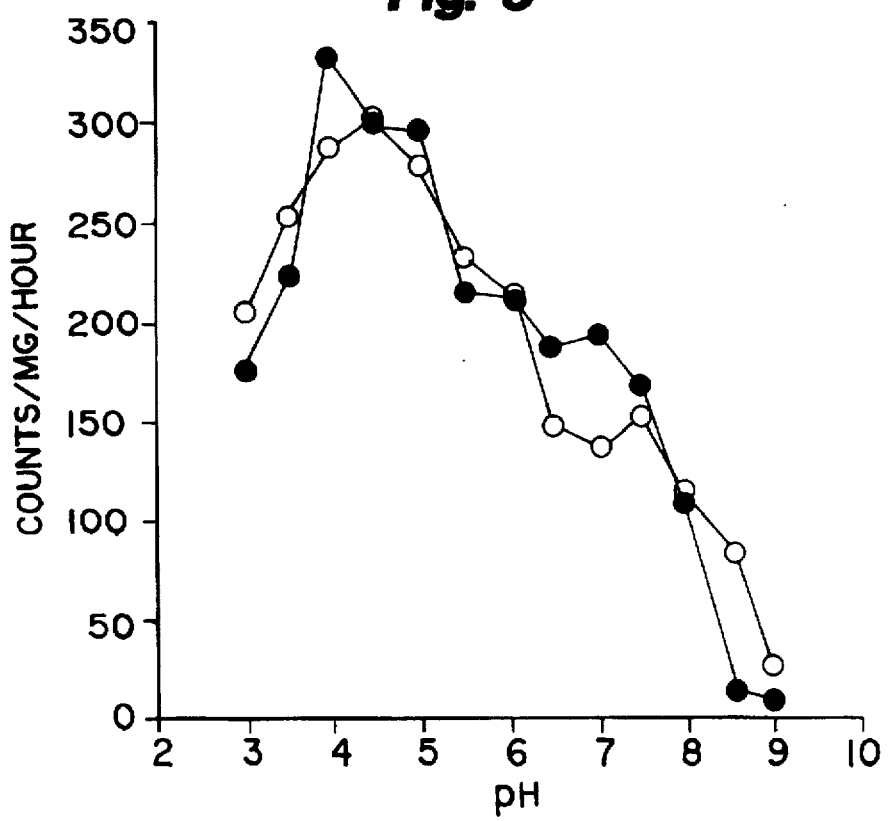
FIG. 9 is a graph showing the pH dependence of $^{125}$I-βA(1–40)-OH deposition onto ceilan katia yarn (silk). ● raw data; ○ data corrected for small differences in peptide concentrations across the indicated pH range.

FIG. 9 shows the pH dependence of $^{125}$I-βA(1–40)-OH deposition onto celian katia yarn. The pH optimum is around pH 5, slightly higher than that observed for deposition onto plaques in AD tissue. However, the important point is that both processes are pH dependent, and both are active in the physiological pH range (pH 5 to 9).

With respect to the impact of detergent on amyloid peptide deposition onto ceilan katia yarn, only the anionic detergent, SDS, affected the rate of binding. Surprisingly, SDS worked to increase binding rate. This is in direct conflict with the hypothesis currently held in the art that the process of amyloid peptide deposition is driven by the hydrophobicity of the carboxyl terminus of the β-amyloid peptide (J. T. Jarrett et al., Biochemistry, 32, 4693–4697 (1993)), since hydrophobicity-driven processes are inhibited by detergents.

Thus, deposition of radiolabelled β-amyloid peptide onto silk and onto AD brain homogenates were both shown to take place from the same solutions, and over a wide range of pH, temperature, metal ions, detergents, etc., both assays give the same qualitative results. For example, in the silk assay, as in the AD tissue assay, the amyloid fragment βA(26–42)-NH$_2$ is more active than βA(1–40)-OH, which in turn is more active than βA(10–35)-NH$_2$. Similarly, Zn(II) accelerates deposition of $^{125}$I-βA(1–40)-OH onto silk thread by a factor of about 5, similar to the enhancement seen with respect to deposition of $^{125}$I-βA(1–40)-OH onto AD plaques. In contrast, deposition of $^{125}$I-βA(26–42)-NH$_2$ onto either silk or AD plaques is unaffected by zinc, presumably because this C-terminal fragment does not contain the histadyl residues responsible for chelating the zinc. At 0.1 nM concentration of β-amyloid peptide (a concentration well below that previously accessible in the prior art, and one that is physiologically relevant), $^{125}$I-labelled human β-amyloid peptide [βA4(1–40)-OH] deposited onto silks at a rate of 20 to 200 cpm per mg silk per hour. Thus, very small amounts of silk can be used for screening large numbers of candidate compound for inhibition of deposition.

EXAMPLE 7

ACTIVITY AND SOLUTION STRUCTURE OF β-AMYLOID PEPTIDE FRAGMENT βA(10–35)-NH$_2$

Methods

Labelled fragments of β-amyloid peptide (βA(10–35)-NH$_2$ and βA(1–28)-OH) were synthesized as described in Example 1. Briefly peptides were purchased or synthesized by fluorenemethoxycarbonyl chemistry on polystyrene resins, using acid-labile blocking groups for sidechain protection, cleaved with trifluoroacetic acid, and purified by RP-HPLC. Final products were>98% pure by HPLC and gave satisfactory amino acid analyses and mass spectra. Plaque deposition assays were conducted using these fragments and the full length 40-mer (βA(1–40)-OH) found in normal cerebrospinal fluid. After radiolabelling to a specific activity of 2000 Ci/mmol, peptides were applied to brain sections as described for two hours; deposition is linear for greater than 24 hours. Autoradiograms were quantitated by densitometry. Under these conditions, βA(1–42) -OH and βA(1–40)-OH were not significantly different. To study the peptide fragments in water we developed a novel approach, measuring NMR data at 750 MHz using a prototype 10 mm $^1$H pulsed field gradient probe. Modified two-dimensional homonuclear TOCSY and NOESY experiments were measured at several pH values and structural information was derived using standard methods.

Briefly, NMR samples of the two peptides were prepared in 90% H$_2$O/10% D$_2$O and the pH adjusted with NaOD.

Peptide concentrations were between 250 and 300 μM. All spectra were recorded at 10° C. Data were acquired on a UNITYplus 750 MHz spectrometer using a prototype 10 mm probe equipped with a pulsed field gradient accessory. To achieve high sensitivity and selective solvent suppression with a 10 mm sample the NOESY pulse sequence was modified to include a selective gradient refocused echo as the read pulse. Additional gradient pulses were added at the beginning of the relaxation delay and on either side of a composite 180 degree pulse located at the center of the NOESY mixing period. The relaxation delay and the NOESY mixing time were set to 1.0 and 0.150 seconds, respectively. Spectral widths were set to 8000 Hz in F2 and F1 with 4096 and 512 complex points, respectively. 256 transients were averaged for a total acquisition time of approximately 50 hours. Data was processed using standard VNMR4.3A software.

In determining the solution structure of $\beta A(10-35)-NH^2$, approximately 150 medium (i+1 to i+3) and long range ($\geq$i+4) NOE constraints were tabulated. 45 medium range and 15 long range unambiguously assigned distance constraints were combined with 8 dihedral angles derived from $^3J_{HNH\alpha}$ coupling constants (FIG. 10) and used in structure calculations. The majority of the applied constraints are localized within the region of the turn-strand-turn motif. RMSD for the backbone from Leu 17 to Ala21, including the sidechains of Val18 and Phe19 was less than 0.43 Ångstroms. The side chains of His14 and Glu22 are also well resolved. Isotope-filtered NOESY experiments are currently underway to further refine the complete solution conformation of $\beta A(10-35)-NH_2$.

The inactive fragment $\beta A(1-28)-OH$ did not exhibit significant secondary structure at several pH values, consistent with previous circular dichroism studies.

Figure 10:
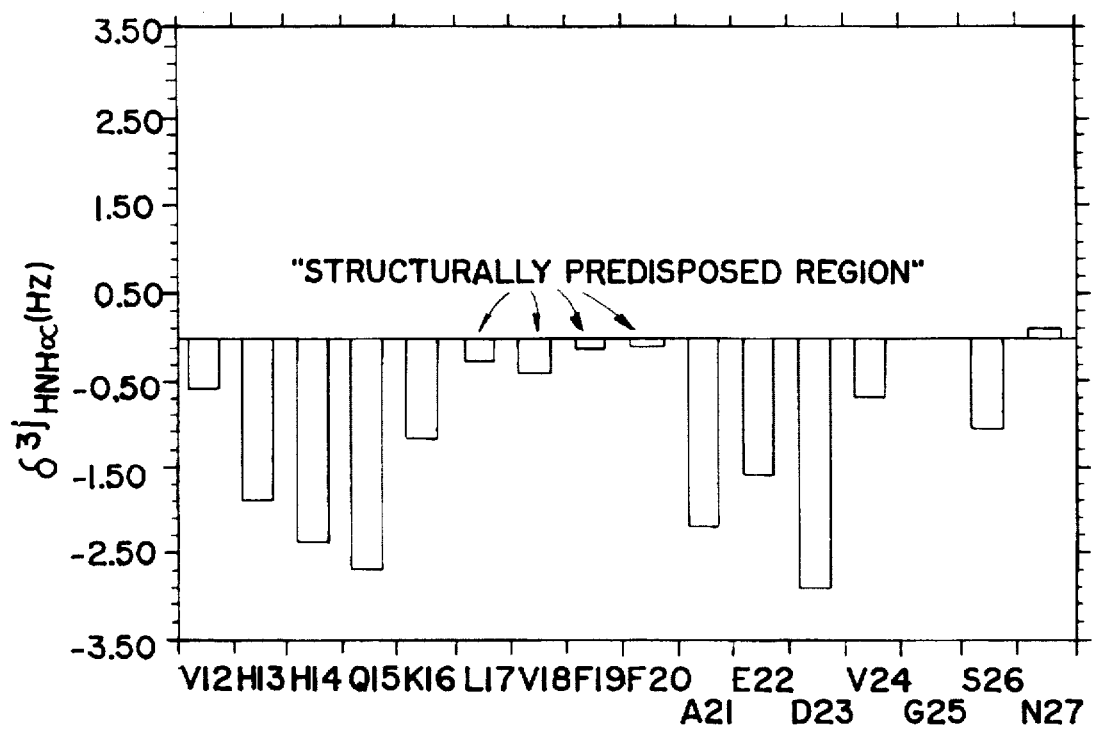
FIG. 10 shows changes in $^3J_{HNH\alpha}$ coupling constants for $^{125}$βA(10–35)-NH$_2$ within the region Glu11 to Asn27 as the pH is raised from 4.1 to 5.7. The region Leu17-Val18-Phe19-Phe20 remains invariant with values of ~8 Hz, while "random coil" values (~5–6 Hz) for the flanking regions decrease significantly into the range of 3.5–4.6 Hz as pH is increased. Values for coupling constants were uncorrected for linewidth. NMR data acquisition is described in the legend of FIG. 12. The data show a pH-dependent conformational change.
Figure 11A:
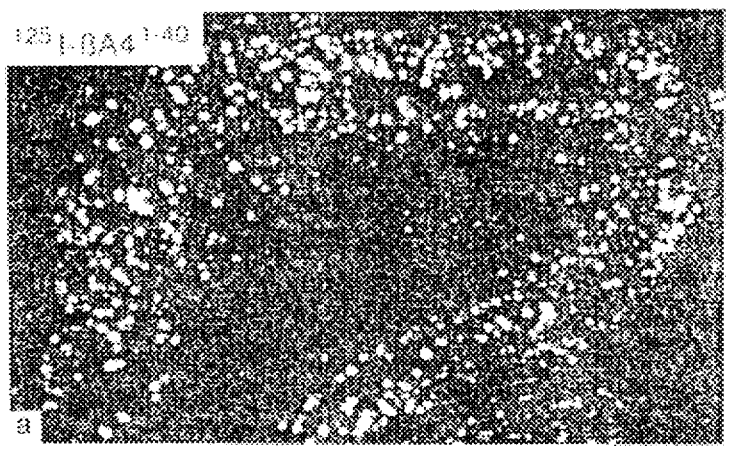
FIG. 11a–11d show deposition of $^{125}$I-labelled human β-amyloid peptides onto plaques in thin sections of frontal cortex from AD brain at pH 7.4. Essentially no deposition is seen in the presence of excess unlabelled peptide. Deposition reflects growth of AD plaques rather than binding to a saturable receptor. Peptides were applied to tissue sections at the same concentration ($10^{-10}$M) and specific activity (2000 Ci/mmol), and labelled at the same amino acid residue (Tyr10). Exposure times for darkfield autoradiography are identical. 11a: $^{125}$I-βA(1–40)-OH), 11b: $^{125}$I-βA(10–35)-NH$_2$, 11c: $^{125}$I-βA(1–28)-OH), 11b: $^{125}$I-βA(10–35)-NH$_2$, 11c: $^{125}$I-βA(1–28)-OH, 11d: Results from quantitation of FIG. 11a–c. Binding reflects the rate of deposition onto AD plaques. Linebar for a–c: 1.9 mm.
Figure 11B:
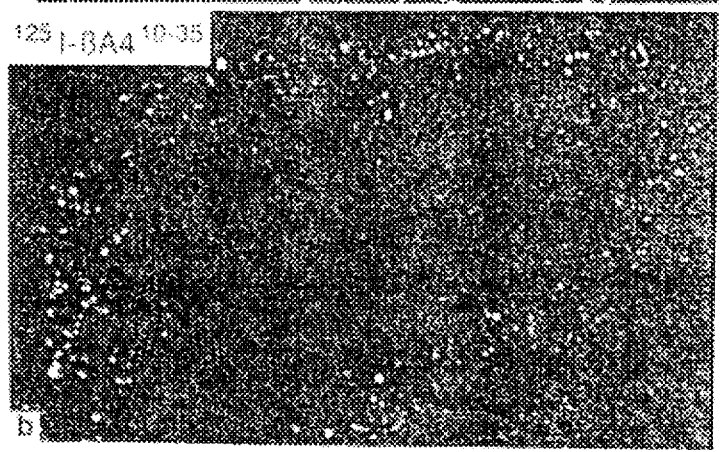
Figure 11C:
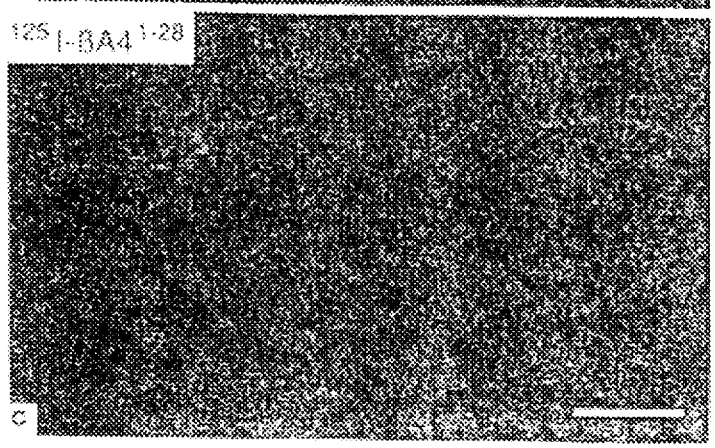
Figure 11D:
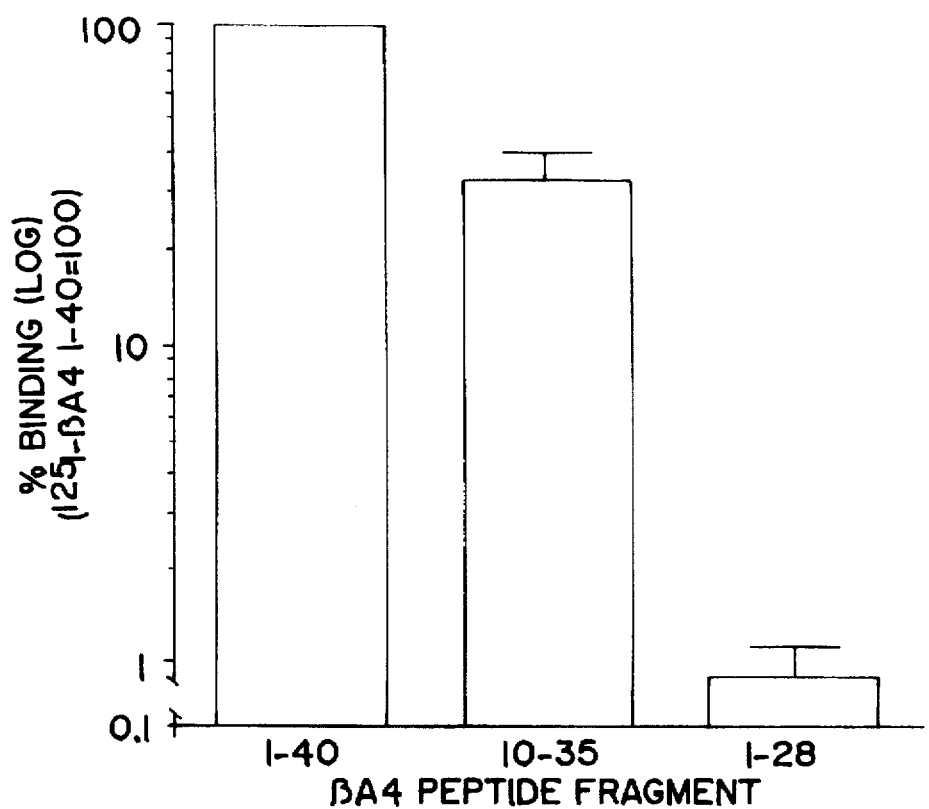
Figure 12A:
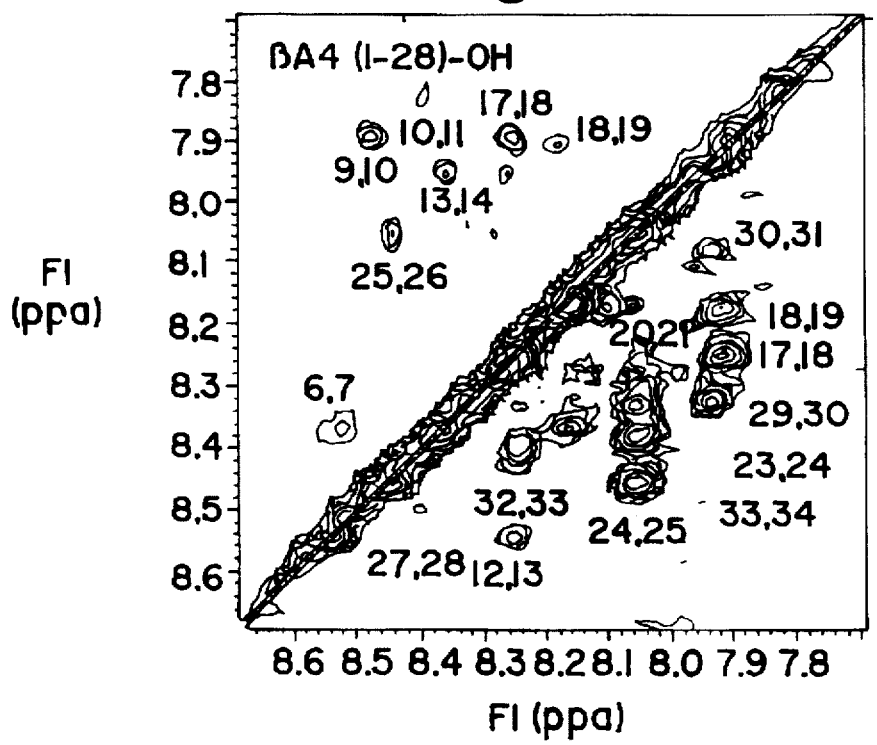
FIG. 12a is a comparison of 2D-NOESY data for βA(10–35)-NH$_2$ and βA(1–28)-OH at pH 5.7. Spectra were acquired, processed, and plotted identically. The NH—NH region of the spectrum for βA(1–28)-OH is above the diagonal. The NH—NH crosspeaks are relatively weak and sparse. They have been assigned between sequential residue pairs His6-Asp7, Gly9-Tyr10, Tyr10-Glu11, Val12-His13, His13-His14, Val18-Phe19, and Gly25-Ser26 as indicated. Below the diagonal are the NH—NH crosspeaks for βA(10–35)-NH$_2$. The number and intensity of cross peaks is significantly greater. Prominent sequential NH—NH connectivities are assigned between Leu 17-Val18, Val18-Phe 19, Phe20-Ala21, Asp23-Val24, Val24-Gly25, Asn27-Lys28, Gly29-Ala30, Ala30-Ile31, Ile32-Gly33, and Gly33-Leu34. The sharp contrast between the two spectra is evidence for the folded nature of βA(10–35)-NH$_2$ in contrast to the relatively unfolded βA(1–28)-OH.

The active fragment $\beta A(10-35)-NH_2$ exhibited a global conformational change as pH was raised from 4 towards 5.7. Above pH 5, the peptide assumed a folded structure and simultaneously became plaque-competent (FIGS. 10 and 11). During this pH-dependent folding transition, the structurally predisposed region Leu17 to Phe20 showed little change in $^3J$ coupling constants, while the flanking regions His14-Gln15-Lys16 and Ala21-Glu22-Asp23 assumed $^3J$ coupling values of 3.5–4.6 Hz at pH 5.7. The small $^3J$ coupling values of these flanking regions indicate that a turn exists on either side of the extended strand found for the Leu17 to Phe20 region. Together these secondary structure elements define a "turn-strand-turn" motif resembling a distorted horseshoe. Many nonsequential internuclear distances can be determined for the folded $\beta A$ fragment above pH 5 via newly appearing Nuclear Overhauser Enhancement (NOE) cross peaks within the 2D-NOESY spectrum (FIG. 12). NOEs between the side chains of His14(+) and Glu22 (−) further support the existence of a turn-strand-turn motif and suggest an intramolecular salt bridge. Intermolecular salt bridges between these two residues have been proposed between adjacent $\beta A$ molecules within AD plaques. In the early onset cerebral amyloidosis of Dutch type, a point mutation changes the wild type Glu22 to Gln22 in $\beta A$; the resulting absence of the putative salt bridge may contribute to the pathology of this hereditary disease.

Figure 13:
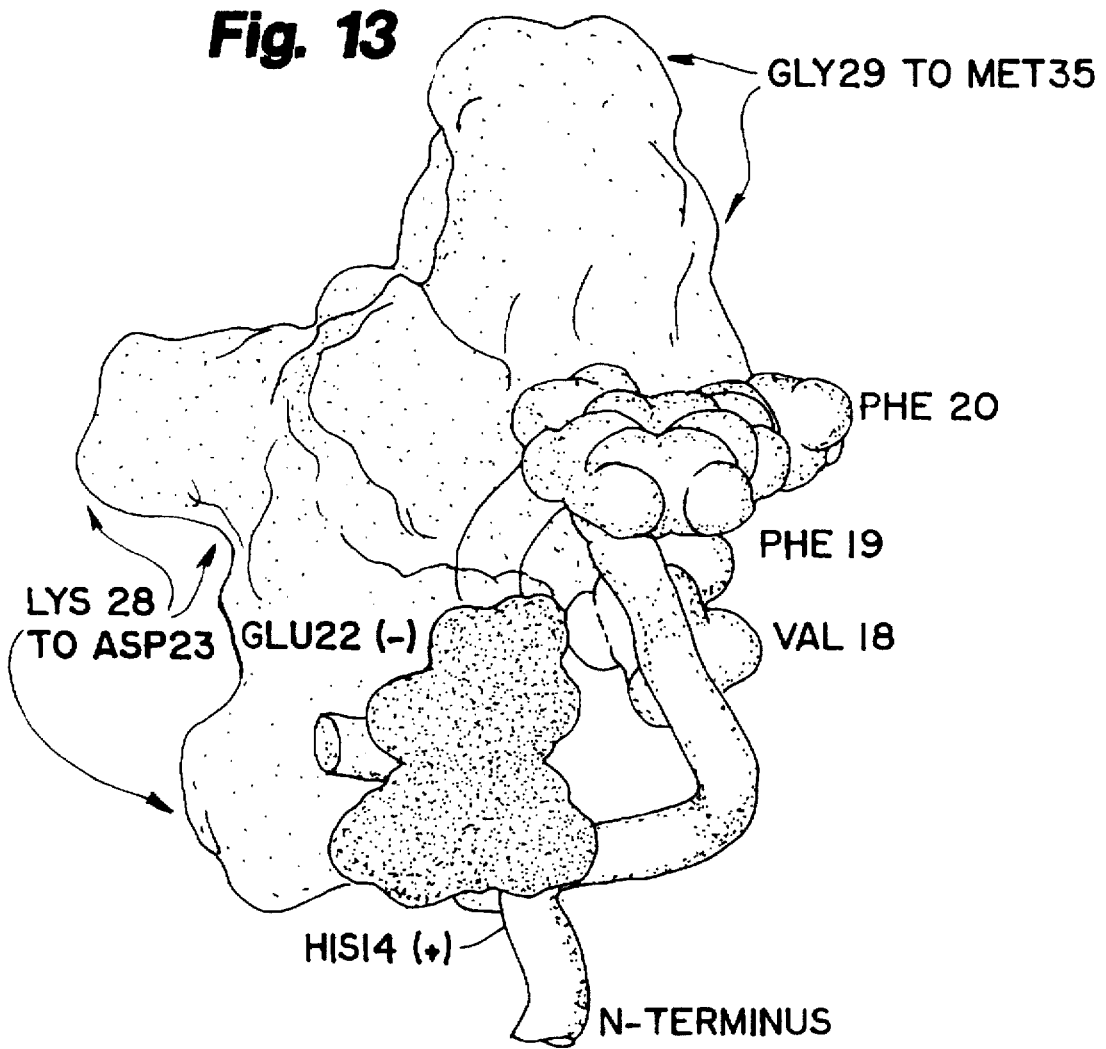
FIG. 13 is computer generated graphical representation of three-dimensional solution conformation of plaque-competent βA(10–35)-NH$_2$ in water at pH 5.7. Proceeding from the N-TERMINUS (bottom) the polypeptide backbone (RIBBON) of the polar residues H$_2$N-Tyr10-Glu11-Val12-His13 [SEQ ID No.: 19] is extended. The residues His14-Gln15-Lys16 create a turn, followed by the conformationally restricted region Leu17-Val18-Phe19-Phe 20 [SEQ ID NO:10] which is extended into a short β-like strand, and then by a second turn created by the Ala21-Glu22-Asp23 region. The close positioning of the sidechains of Glu22(–) and His14(+) (darkly shaded spheres) suggest the existence of a salt bridge within the structure. The remainder of the peptide is represented as surfaces to indicate approximate orientation of these residues relative to the turn-strand-turn motif. Residues Val24-Gly25-Asn26-Ser27-Lys28 [SEQ NO:11] rise up the left side of the turn-strand-turn motif. Residues Gly29-Ala30-Ile31-Ile32-Gly33-Leu34-Met35 [SEQ ID No:12] of the hydrophobic carboxyl terminus shown at the top of the figure. Stabilization of this conformation is likely to depend upon the burying of the hydrophobic residues of the short strand under residues from the carboxyl terminus and may be further stabilized by anchoring together both sides of the turn-strand-turn motif via a salt bridge. The structural information presented is the average result of 40 calculated structures.

The conformation of $\beta A(10-35)-NH_2$ in aqueous solution was found to be devoid of α-helix or β-sheet (FIG. 13). Several i to i+2 interresidue NOEs within the region from Tyr10 to His13 suggest that the amino terminus is extended. The turn-strand-turn motif for residues His14 to Asp23 is partially stabilized through interactions between the sidechains of the Leu17-Phe20 strand and hydrophobic residues from the C-terminal Gly29-Met35 region.

Results

The 26 residue fragment $\beta A(10-35)-NH_2$ is plaque-competent, displaying about 35% of the activity of the full length peptide. As $\beta A(10-35)-NH_2$ is derived from the central region of the $\beta A$ sequence, these data indicate that neither the amino-terminal nine nor carboxyl terminal five residues of $\beta A(1-40)-\alpha-1$ are necessary for activity or folding; $\beta A(10-35)-NH_2$ is both folding-competent and plaque-competent. Consequently, $\beta A(10-35)-NH_2$ presents a reasonable model system for investigating the amyloidogenic structure/activity relationship of the full length peptide ($\beta A(1-40)-OH$. In contrast, a 28 residue fragment $\beta A(1-28)-OH$, corresponding to the amino terminal region, has no detectable activity (less than 1% of the activity of $\beta A(1-40)-OH$).

Growth of tissue plaques by deposition of labelled peptides from solution was found to be pH-dependent (FIG. 10). All $\beta A$ fragments examined to date were unable to support plaque growth below pH 4, while active fragments such as $\beta A(1-40)-OH$ and $\beta A(10-35)-NH_2$ are plaque-competent within the pH range of 5 to 9. In contrast, the plaque-incompetent fragment $\beta A(1-28)-OH$ was inactive at all pH values tested.

A computer generated model of the solution structure of $\beta A(10-35)-NH_2$ is shown in FIG. 13.

The invention has been described with reference to various specific and preferred embodiments and techniques. However, it should be understood that many variations and modifications may be made while remaining within the spirit and scope of the invention.

---

What is claimed is:

1. An in vitro method of screening an agent capable of affecting the deposition of β-amyloid peptide or peptide fragment thereof on tissue, comprising:
   (a) combining a sample of silk with an amount of a labelled β-amyloid peptide or labelled active peptide fragment thereof, effective to bind with a tissue evidencing the presence of, amyloidosis, and with a potential deposition-affecting agent to be screened, for a time effective to allow binding of the labelled peptide or peptide fragment to the silk;
   (b) detecting the amount of labelled peptide or the labelled active peptide fragment thereof bound to the silk; and
   (c) assessing the effect of the agent on the deposition of the β-amyloid peptide or peptide fragment.

2. The method of claim 1 wherein the concentration of labelled β-amyloid peptide or labelled active peptide fragment thereof is subnanomolar.

3. The method of claim 1, wherein the silk is spider silk or silkworm silk.

4. The method of claim 1, wherein the silk is a commercially available silk fabric.

5. The method of claim 4 wherein the silk fabric is selected from the group consisting of:
   (a) raw silk;
   (b) organza;
   (c) natural tan pongee;
   (d) doupioni cloth; and
   (e) ceilan katia yarn.

6. The method of claim 5 wherein the silk fabric is ceilan katia yarn.

7. The method according to claim 1, wherein the label of the (β-amyloid peptide or the active peptide fragment thereof is a radioactive label, an enzymatic label, fluorescent label or an antigenic label.

8. The method of claim 1, wherein said active peptide fragment is selected from the group consisting of:

(a) βA(26–42)-NH$_2$, wherein βA(26–42) has the amino acid sequence set forth in SEQ ID NO:4, (b) βA(1–40)-NH$_2$, wherein βA(1–40) has the amino acid sequence set forth in SEQ ID NO:1, (c) βA(1–40)-PEG, wherein βA(1–40) has the amino acid sequence set forth in SEQ ID NO:1, (d) (des-A2)-βA(1–40), wherein (des-A2)-βA(1–40) has the amino acid sequence set forth in SEQ ID NO:5, (e) βA(1–35)-NH$_2$, wherein βA(1–35) has the amino acid sequence set forth in SEQ ID NO:6, (f) βA(10–35)-NH$_2$, wherein βA(10–35) has the amino acid sequence set forth in SEQ ID NO:7, (g) βA(10–35), wherein βA(10–35) has the amino acid sequence set forth in SEQ ID NO:7, (h) Q22-βA(1–40), wherein Q22-βA(1–40) has the amino acid sequence set forth in SEQ ID NO:8, and (i) βDA(1–42), wherein βA(1–42) has the amino acid sequence set forth in SEQ ID NO:2.

9. The method of claim 8, wherein said active peptide fragment is selected from the group consisting of:

(a) βA(26–42)-NH$_2$, wherein βA(26–42) has the amino acid sequence set forth in SEQ ID NO:4, and (b) βA(10–35)-NH$_2$, wherein β(10–35) has the amino acid sequence set forth in SEQ ID NO:7.

* * * * *

UNITED STATES PATENT AND TRADEMARK OFFICE
CERTIFICATE OF CORRECTION

PATENT NO. : 5,721,106
DATED : February 24, 1998
INVENTOR(S) : John E. Maggio, et. al.

It is certified that error appears in the above-identified patent and that said Letters Patent is hereby corrected as shown below:

Col. 4, line 22, delete "↑" and insert --□--;

Col. 9, line 9, delete "β3A(25-35)-NH$_2$" and insert --βA(25-35)-NH$_2$--;

Col. 9, lines 20-21, delete "peptide$^{10-}_{35}$-NH$_2$" and insert --peptide$^{10-35}$-NH$_2$--;

Col. 13, line 26, delete "Iβ-amyloid" and insert --β-amyloid--;

Col. 18, line 33, delete "200.000 dpm/μl" and insert --200,000 dpm/μl--;

Col. 33, line 56, delete "of, amyloidosis" and insert --of amyloidosis--;

Col. 33, line 59, delete "peptide fragment to the silk;" and insert --the labelled active peptide fragment thereof to the silk;--

Col. 33, line 60-62, delete "detecting the amount of labelled peptide or the labelled active peptide fragment thereof bound to the silk; and" and insert --detecting the amount of labelled peptide or peptide fragment bound to the silk; and--;

Col. 34, line 65, delete "(β-amyloid" and insert --β-amyloid--;

Col. 34, line 66, delete "an enzymatic label" and insert --and enzymatic label--; and Col. 36, line 5, delete "βDA(1-42)" and insert --βA(1-42)--.

Signed and Sealed this

Sixth Day of February, 2001

Attest:

Attesting Officer

Q. TODD DICKINSON
Director of Patents and Trademarks